(12) United States Patent
Griffin et al.

(10) Patent No.: US 12,154,667 B2
(45) Date of Patent: Nov. 26, 2024

(54) SECURE ENVIRONMENT DEVICE MANAGEMENT

(71) Applicant: International Business Machines Corporation, Armonk, NY (US)

(72) Inventors: Adam L. Griffin, Dubuque, IA (US); Srinivas B. Tummalapenta, Broomfield, CO (US); Nikhilkumar V. Shah, Bear, DE (US); Huyanh D. Ngo, Sterling Heights, MI (US); Paul A. Ragone, Winter Garden, FL (US)

(73) Assignee: International Business Machines Corporation, Armonk, NY (US)

( * ) Notice: Subject to any disclaimer, the term of this patent is extended or adjusted under 35 U.S.C. 154(b) by 717 days.

(21) Appl. No.: 16/437,600

(22) Filed: Jun. 11, 2019

(65) Prior Publication Data

US 2020/0395107 A1 Dec. 17, 2020

(51) Int. Cl.
*G16H 10/65* (2018.01)
*G06F 16/182* (2019.01)
*G08B 21/04* (2006.01)
*H04L 9/06* (2006.01)
*H04L 9/00* (2022.01)

(52) U.S. Cl.
CPC ......... *G16H 10/65* (2018.01); *G06F 16/1824* (2019.01); *G06F 16/1834* (2019.01); *G08B 21/0453* (2013.01); *H04L 9/0643* (2013.01); *H04L 9/50* (2022.05)

(58) Field of Classification Search
CPC ............. G06F 16/1824; G06F 16/1834; G08B 21/0453; H04L 9/0643; H04L 2209/38
See application file for complete search history.

(56) References Cited

U.S. PATENT DOCUMENTS

| | | | |
|---|---|---|---|
| 6,961,448 | B2 | 11/2005 | Nichols et al. |
| 8,131,565 | B2 | 3/2012 | Dicks et al. |
| 9,716,595 | B1 | 7/2017 | Kravitz et al. |
| 10,489,597 | B2 | 11/2019 | Safford |
| 10,552,469 | B2 | 2/2020 | Maybee |

(Continued)

FOREIGN PATENT DOCUMENTS

KR 101868589 B1 6/2018

OTHER PUBLICATIONS

Griggs et al Healthcare Blockchain System Using Smart Contracts for Secure Automated Remote Patient Monitoring, Jun. 2018, J. Med. Sys. 42:130, pp. 1-7 (Year: 2018).*

(Continued)

*Primary Examiner* — Gregory Lultschik
(74) *Attorney, Agent, or Firm* — Aaron N. Pontikos

(57) ABSTRACT

A method controls a modification of an adjustable device. A system establishes a circle of trust for a plurality of devices, where at least one of the plurality of devices is an adjustment control device for adjusting an adjustable device. Operations of the adjustment control device are controlled via a blockchain, where the blockchain must approve the adjustment control device before an adjustment of the adjustable device is performed by the adjustment control device. The system receives an approval from the blockchain for the adjustment control device to adjust the adjustable device, and the adjustment control device adjusts the adjustable device in response to receiving the approval from the blockchain.

20 Claims, 15 Drawing Sheets

(56) References Cited

U.S. PATENT DOCUMENTS

| | | | |
|---|---|---|---|
| 10,944,547 B2 | 3/2021 | Tummalapenta | |
| 11,017,892 B1* | 5/2021 | Knas | G16H 20/10 |
| 2006/0168173 A1* | 7/2006 | Clemm | H04L 41/046 709/223 |
| 2006/0294192 A1 | 12/2006 | Mao | |
| 2008/0046039 A1 | 5/2008 | Corndorf | |
| 2008/0215509 A1 | 9/2008 | Charlton | |
| 2008/0235733 A1 | 9/2008 | Heie et al. | |
| 2008/0265733 A1 | 10/2008 | Hue | |
| 2013/0185783 A1* | 7/2013 | Jelatis | G16Z 99/00 726/7 |
| 2013/0212161 A1 | 8/2013 | Ben-Shaul et al. | |
| 2014/0033226 A1 | 1/2014 | Glazer | |
| 2014/0053226 A1 | 2/2014 | Fadida et al. | |
| 2014/0258405 A1 | 9/2014 | Perkin | |
| 2014/0281489 A1 | 9/2014 | Peterka et al. | |
| 2014/0304773 A1* | 10/2014 | Woods | H04L 63/08 726/3 |
| 2015/0032838 A1 | 1/2015 | Demsey | |
| 2015/0165118 A1* | 6/2015 | Lee | A61M 5/14228 604/67 |
| 2016/0012249 A1* | 1/2016 | Keppler | G16H 40/67 726/28 |
| 2016/0080149 A1 | 3/2016 | Mehta | |
| 2016/0080474 A1 | 3/2016 | Argenti | |
| 2016/0210626 A1 | 7/2016 | Ortiz et al. | |
| 2016/0216955 A1 | 7/2016 | Kwon | |
| 2017/0065823 A1 | 3/2017 | Kaib et al. | |
| 2017/0140145 A1 | 5/2017 | Shah | |
| 2017/0150939 A1 | 6/2017 | Shah | |
| 2017/0173262 A1 | 6/2017 | Veltz | |
| 2017/0177898 A1 | 6/2017 | Dillenberger | |
| 2017/0300627 A1* | 10/2017 | Giordano | G06F 21/6245 |
| 2017/0317824 A1 | 11/2017 | Brown | |
| 2018/0039667 A1 | 2/2018 | Pierce et al. | |
| 2018/0189449 A1* | 7/2018 | Karumba | G16H 40/67 |
| 2018/0316502 A1 | 11/2018 | Nadeau | |
| 2019/0200977 A1* | 7/2019 | Shelton, IV | A61B 17/07207 |
| 2019/0207957 A1 | 7/2019 | Espinosa | |
| 2019/0232065 A1* | 8/2019 | Perschbacher | A61N 1/3624 |
| 2019/0258807 A1* | 8/2019 | DiMaggio | G06N 20/00 |
| 2019/0272604 A1 | 9/2019 | Kim | |
| 2019/0298260 A1* | 10/2019 | Yamashita | G16H 10/60 |
| 2019/0349190 A1* | 11/2019 | Smith | H04L 67/562 |
| 2020/0012765 A1 | 1/2020 | Smaiely | |
| 2020/0366653 A1* | 11/2020 | Caceres | H04L 63/0853 |
| 2020/0388385 A1* | 12/2020 | De Los Reyes | G16H 50/70 |
| 2021/0160056 A1* | 5/2021 | Yan | G06F 21/602 |
| 2022/0157143 A1* | 5/2022 | Panneer Selvam | G04G 9/007 |

OTHER PUBLICATIONS

Pham et al A Secure Remote Healthcare System for Hospital Using Blockchain Smart Contract, 2018, 2018 IEEE Globecom Workshops (GC Wkshps), pp. 1-6 (Year: 2018).*

Notice of Allowance for Related U.S. Appl. No. 16/100,513.
Office Action for Related U.S. Appl. No. 26/200,513, filed Mar. 16, 2020.
Amendment Responsive to Mar. 16, 2020 Office Action for Related U.S. Appl. No. 16/100,513, filed Aug. 17, 2020.
"GitHub—mitmedialab/medrec: medical records on the blockchain https://medrec.media.mit.edu/", MedRec, downloaded from the Internet on Jul. 8, 22, 6 pages, <https://github.com/mitmedialab/medrec>.
Davis, Jessica, "Is FDA doing enough to support medical device security?", Aug. 15, 2018, 11 pages.
Nchinda et al., "MedRec: A Network for Personal Information Distribution", 2019 International Conference on Computing, Networking and Communications (ICNC), Feb. 18-21, 2019, Honolulu, HI, USA, DOI: 10.1109/ICCNC.2019.8685631, 5 pages.
Nchinda, Nchinda, "Medrec: Patient Centered Medical Records Using a Distributed Permission Management System", MIT Media Lab, 2018, Thesis, 52 pages, <https://github.com/mitmedialab/medrec/blob/master/paper/Thesis.pdf>.
A. Lipman et al., "Medrec", MIT Media Lab, Viral Communications, <https://www.media.mit.edu/projects/medrec/overview/>, Retrieved Jun. 10, 2019, pp. 1-9.
B. Rios et al., "Understanding Pacemaker Systems Cybersecurity", Whitescope IO, Blog for https://WhiteScope.IO, May 23, 2017, pp. 1-4.
B. Rios et al., "Security Evaluation of the Implantable Cardia Device Ecosystem Architecture and Implementation Interdependencies", Whitescope, May 17, 2017, pp. 1-27.
Medtronic, Inc., "Product Information for Clinicians: Mycarelink Smart TM Monitor 25000, 30100, 30101", Medtronic, 2017, pp. 1-8.
Apple Inc., "Press Release: Apple Watch Series 4: Beautifully Redesigned With Breakthrough Communication, Fitness, and Health Capabilities", apple.com, Sep. 12, 2018, pp. 1-13.
Epripay GMBH, "Gesundheits Card" <www.gesundheitscard.org>, Retrieved Jun. 11, 2019, pp. 1-11.
Anonymous, "Healthcare: E-Health Records", <https://e-estonia.com/solutions/healthcare/e-health-record/> Retrieved Jun. 11, 2019, pp. 1-4.
John D. Halamka et al., "Blockchain Healthcare Today: About the Journal", Blockchain Healthcare Today, blockchainhealthcaretoday.com, Retrieved Jun. 11, 2019, pp. 1-6.
US Dept of Homeland Security NCCIC, "Medtronic 2090 Carelink Programmer Vulnerabilities (Update B)" Advisory (ICSMA-18-058-01), Oct. 11, 2018, US DHS, pp. 1-4.
L. Newman, "A New Pacemaker Hack Puts Malware Directly on The Device", www.wired.com/story/, Aug. 9, 2018, pp. 1-3.
IBM Patents or Patent Applications Treated as Related, Jun. 11, 2019.
P. Mell et al., "The NIST Definition of Cloud Computing", National Institute of Standards and Technology, Information Technology Laboratory, Sep. 2011, pp. 1-7.
Citrix Systems, Inc., "Go Beyond Virtual Desktop Infrastructure (VDI)" <https://www.citrix.com/virtualization/vdi.html>, Retrieved Aug. 10, 2018, pp. 1-4.
PowWow Mobile, "Core Technology", <https://www.powwowmobile.com/core-technology/>, Retrieved Aug. 10, 2018, pp. 1-3.

* cited by examiner

| 402 | 404 | 406 | 408 | 410 | 412 | 414 | 416 | 418 | 420 |
|---|---|---|---|---|---|---|---|---|---|
| SUPERVISORY COMPUTER IDENTIFIER | TRUST CIRCLE ENTITIES IDENTIFIER | JOINT OWNERS IDENTIFIER | SOFTWARE IMAGE(S) | SOFTWARE IMAGE METADATA | ADJUSTABLE DEVICE'S CURRENT STATE | TRANSACTION | LEGAL DOCUMENT | DIGITAL RIGHTS FOR CONTENT | ASSET OWNERSHIP |

SECURE ENVIRONMENT DEVICE MANAGEMENT

BACKGROUND

The present invention relates to the field of hardware devices, and particularly to hardware devices that are connected via a secure environment, such as a blockchain environment. Still more particularly, the present invention relates to modifying adjustable hardware devices via the blockchain environment.

SUMMARY

In one or more embodiments of the present invention, a method controls a modification of an adjustable device. A system establishes a circle of trust for a plurality of devices, where at least one of the plurality of devices is an adjustment control device for adjusting an adjustable device. Operations of the adjustment control device are controlled via a blockchain, where the blockchain must approve the adjustment control device before an adjustment of the adjustable device is performed by the adjustment control device. The system receives an approval from the blockchain for the adjustment control device to adjust the adjustable device, and the adjustment control device adjusts the adjustable device in response to receiving the approval from the blockchain.

In one or more embodiments of the present invention, the method(s) described above are implemented as a computer system and/or as a computer program product.

BRIEF DESCRIPTION OF THE DRAWINGS

FIG. 4 depicts an exemplary blockchain ledger as used in one or more embodiments of the present invention;

DETAILED DESCRIPTION

Figure 1:
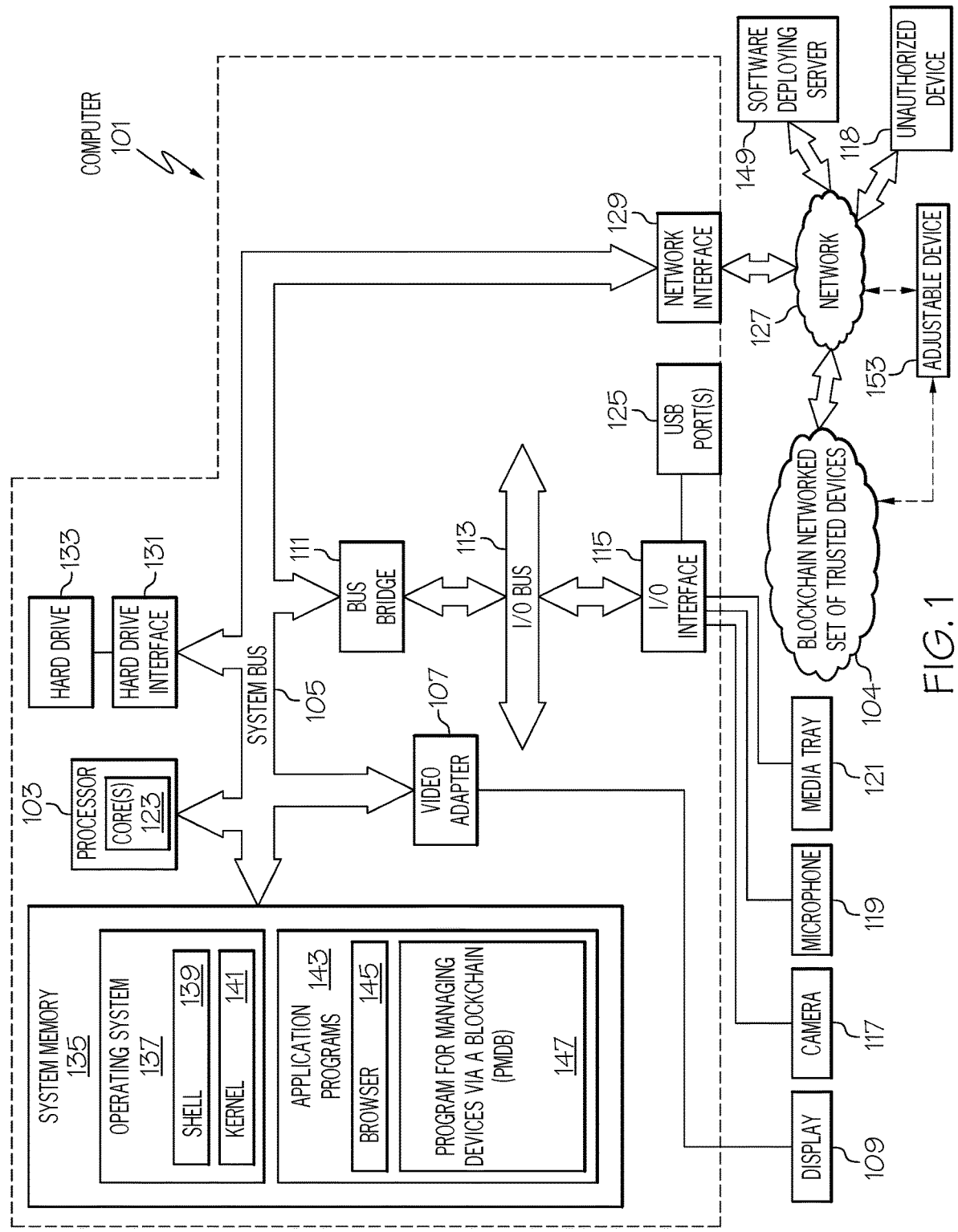
FIG. 1 depicts an exemplary system and network that is used in one or more embodiments of the present invention.

In one or more embodiments, the present invention is a system, a method, and/or a computer program product at any possible technical detail level of integration. In one or more embodiments, the computer program product includes a computer readable storage medium (or media) having computer readable program instructions thereon for causing a processor to carry out aspects of the present invention.

The computer readable storage medium is a tangible device that is able to retain and store instructions for use by an instruction execution device. In one or more embodiments, the computer is, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein are capable of being downloaded to respective computing/processing devices from a computer readable storage medium or to an external computer or external storage device via a network, for example, the Internet, a local area network, a wide area network and/or a wireless network. In one or more embodiments, the network comprises copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

In one or more embodiments, computer readable program instructions for carrying out operations of the present invention comprise assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. In one or more embodiments, the computer readable program instructions execute entirely on the user's computer, partly on the user's computer, as a stand-alone software package, partly on the user's computer and partly on a remote computer or entirely on the remote computer or server. In the latter scenario and in one or more embodiments, the remote computer connects to the user's computer through any type of network, including a local area network (LAN) or a wide area network (WAN), or the connection is made to an external computer (for example, through the Internet using an Internet Service Provider). In some embodiments, electronic circuitry including, for example, programmable logic circuitry, field-programmable gate arrays (FPGA), or programmable logic arrays (PLA) execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, are implemented by computer readable program instructions in one or more embodiments of the present invention.

In one or more embodiments, these computer readable program instructions are provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In one or more embodiments, these computer readable program instructions are also stored in a computer readable storage medium that, in one or more embodiments, directs a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

In one or more embodiments, the computer readable program instructions are also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams represents a module, segment, or portion of instructions, which comprises one or more executable instructions for implementing the specified logical function(s). In some alternative implementations, the functions noted in the block occur out of the order noted in the figures. For example, two blocks shown in succession are, in fact, executed substantially concurrently, or the blocks are sometimes executed in the reverse order, depending upon the functionality involved. It will also be noted that, in one or more embodiments of the present invention, each block of the block diagrams and/or flowchart illustration, and combinations of blocks in the block diagrams and/or flowchart illustration, are implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that are utilized in the one or more embodiments of the present invention. In accordance with various embodiments of the present invention, some or all of the exemplary architecture, including both depicted hardware and software, shown for and within computer 101 utilized by software deploying server 149 and/or devices within a blockchain networked Set of Trusted Devices 104 and/or adjustable device 153 shown in FIG. 1, one or more of the devices shown in the circle of trust 204 in FIG. 2, one or more of the processing nodes shown in the blockchain environment 300 in FIG. 3, one or more of the peers shown in the blockchain fabric 600 depicted in FIG. 6, one or more of the devices shown in the circle of trust 904 in FIG. 9, one or more of the devices shown in the circle of trust 1004 in FIG. 10, and/or one or more of the devices shown in FIG. 11.

In one or more embodiments of the present invention, exemplary computer 101 includes a processor 103 that is coupled to a system bus 105. Processor 103 utilizes one or more processors, each of which has one or more processor cores 123. A video adapter 107, which drives/supports a display 109 (which in one embodiment is a touch-screen display capable of detecting touch inputs onto the display 109), is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a keyboard 117, a microphone 119, a media tray 121 (which in one embodiment includes storage devices such as CD-ROM drives, multi-media interfaces, etc.), and external USB port(s) 125. While the format of the ports connected to I/O interface 115 is that which is known to those skilled in the art of computer architecture, including by not limited to universal serial bus (USB) ports.

As depicted, computer 101 is able to communicate with a software deploying server 149 and/or other devices/systems using a network interface 129. Network interface 129 is a hardware network interface, such as a network interface card (NIC), etc. In one or more embodiments, network 127 is an external network such as the Internet, or an internal network such as an Ethernet or a virtual private network (VPN). In one or more embodiments, network 127 is a wireless network, such as a Wi-Fi network, a cellular network, etc. As such, computer 101 and/or blockchain-networked Set of Trusted Devices 104 are devices capable of transmitting and/or receiving wireless and/or wired communications.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include a Program for Managing Devices via a Blockchain (PMDB) 147. PMDB 147 includes code for implementing the processes described below, including those described in FIGS. 2-13. In one embodiment, computer 101 is able to download PMDB 147 from software deploying server 149, including in an on-demand basis, wherein the code in PMDB 147 is not downloaded until needed for execution. In one embodiment of the present invention, software deploying server 149 performs all of the functions associated with the present invention (including execution of PMDB 147), thus freeing computer 101 from having to use its own internal computing resources to execute PMDB 147.

Figure 9:
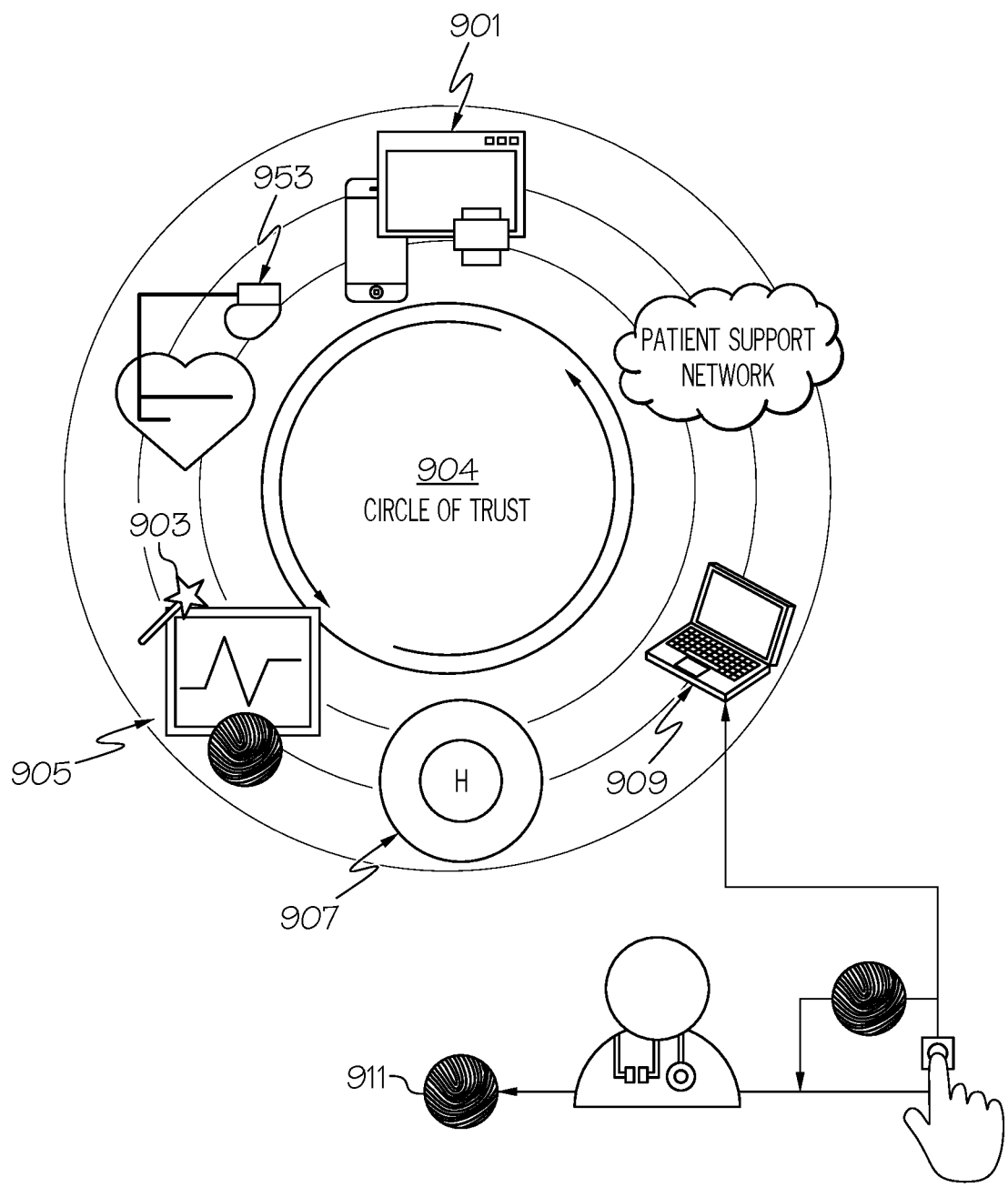
FIG. 9 illustrates detail of circle of trust of devices as used in one or more embodiments of the present invention.

A blockchain networked set of trusted devices 104 includes one or more physical devices (see FIG. 9) that are able to be adjusted/programmed by an adjustable device, which in an embodiment of the present invention is part of the circle of trust depicted in FIG. 9, and in another embodiment of the present invention is outside of the circle of trust, as illustrated by the adjustable device 153 shown in FIG. 1. In an embodiment of the present invention, computer 101 is part of the blockchain networked set of trusted devices 104.

As used herein, the terms "blockchain", "blockchain environment", "blockchain system", and "blockchain fabric" are used interchangeably to describe a system that utilizes a collection of processing devices that support a distributed system that securely controls a ledger of transactions described in a series of "blocks" (collectively also called a "blockchain"). Details of an exemplary "blockchain", "blockchain environment", "blockchain system", "blockchain fabric", etc. as used to describe a system of devices are described in detail below in FIG. 3 and FIG. 6-7. Details of an exemplary "blockchain" as used to describe a collection of transaction blocks are described in detail below in FIG. 4 and FIG. 11.

The hardware elements depicted in computer 101 are not intended to be exhaustive, but rather are representative to highlight essential components required by the present invention. For instance, in one or more embodiments computer 101 includes alternate memory storage devices such as magnetic cassettes, digital versatile disks (DVDs), Bernoulli cartridges, and the like. These and other variations are intended to be within the spirit and scope of the present invention.

Personal medical device security is an important issue, both from the privacy issue as well as the performance issue of medical devices. That is, if a medical device (e.g., a pacemaker) is open to unlimited access (via the internet, close-range electronic communications, etc.), then not only does this expose it to hacking of the data that it contains, but also exposes it to hacking the operations of the device (e.g., reprogramming the device to perform a different function).

In order to address this issue, one or more embodiments of the present invention present a novel technical blockchain evolution built on circles of trust that encapsulate and encompass authenticated medical devices and/or nodes to perform functions that relate to patient needs.

Figure 10:
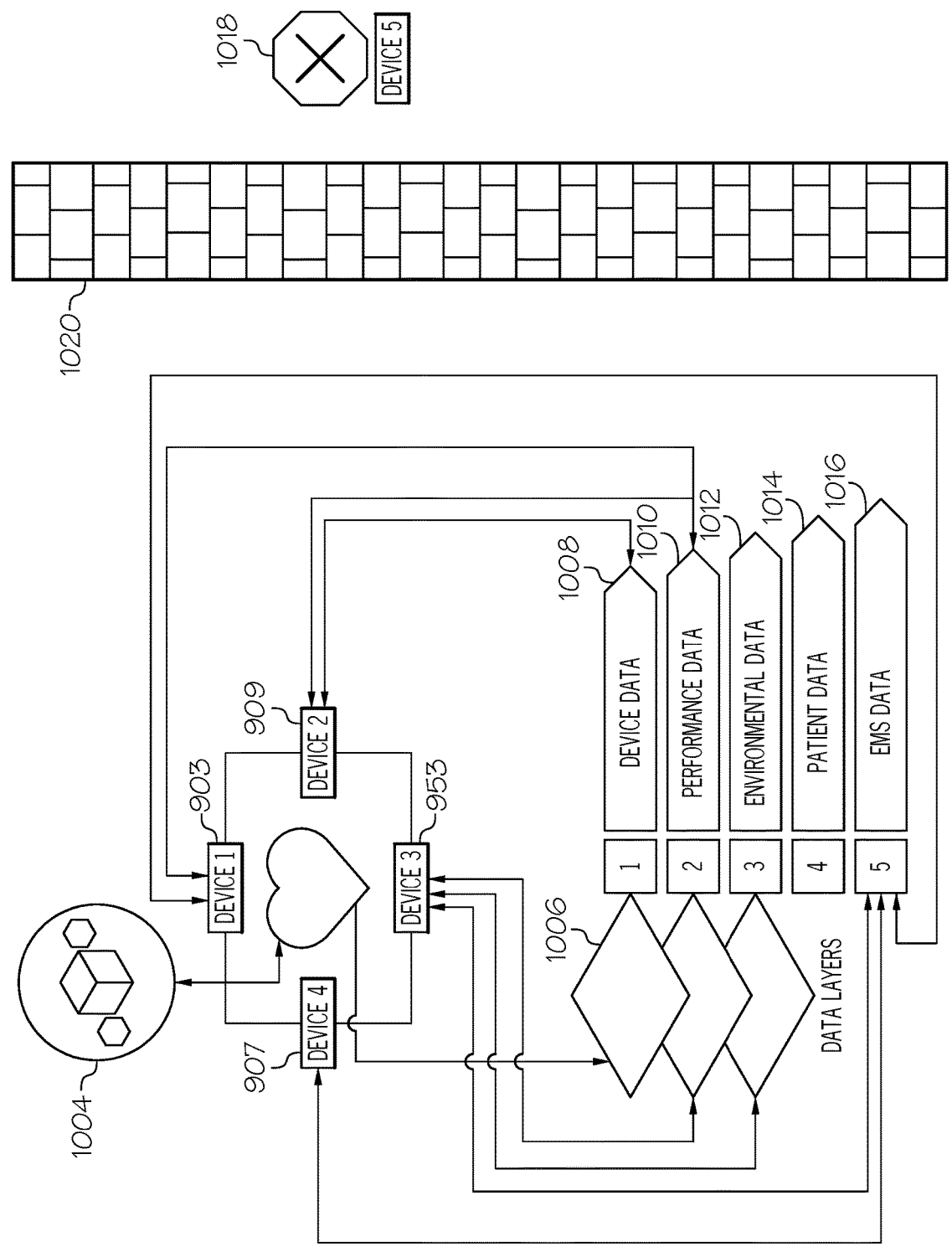
FIG. 10 depicts additional detail of a circle of trust of devices as used in one or more embodiments of the present invention.

As described herein in one or more embodiments of the present invention, the system shares data represented as data layers in FIG. 10 with role-defined and justified persons of need to be known within the trusted medical circle relationship.

In an embodiment of the present invention, encryption and/or biometric identity-validation processes control which adjustable device can be adjusted and/or which adjustment control device does this adjusting. That is, before an adjustable device (e.g., a pacemaker) can be adjusted by an adjustment control device (e.g., computer 101, which in an embodiment of the present invention is part of the blockchain networked set of trusted devices 104 shown in FIG. 1), such an adjustment must be authorized/authenticated by a circle of trust of trusted devices as described herein (see FIG. 2).

As an example of the problem that the present invention addresses, consider a patient who has a pacemaker. Medical device programming devices that can reprogram the pacemaker are available to the public, often without any requirement that the user have a medical license, a background in programming, etc. Thus, the pacemaker becomes ineffective, if not dangerous, to the patient, since it can be modified in a manner that it was not programmed for based on this patient's particular medical condition. In order to ensure that such changes are made by qualified and competent actors, the present invention utilizes a circle of trust of trusted devices that can be used to modify the pacemaker. If the patient is qualified to modify the pacemaker, even if it is his/her own, then the patient will petition for his/her programming device to be part of the circle of trust, thus enabling him/her with the ability to reprogram the pacemaker. That is, the circle of trust only permits devices approved in the circle to "talk/share" with each other. As such, any accepted member of the circle of trust is allowed to communicate with other devices within the circle of trust.

As described herein, one or more embodiments of the present invention present a method and system for utilizing a blockchain to control and protect data layers within an adjustable device in order to protect the data within that adjustable device and/or to protect the functionality of that adjustable device (e.g., to prevent improper modification of the adjustable device).

In order to address the problem stated above of unauthorized access to adjustable devices (e.g., medical devices such as a pacemaker that controls a rhythm of a heart by providing programmed electrical impulses to the sinoatrial node in the heart), one or more embodiments of the present invention utilize a circle of trust, which in an embodiment of the present invention includes the adjustable device, and in another embodiment of the present invention is coupled to, but does not include, the adjustable device. In either embodiment, the circle of trust addresses issues of Efficiency, Security, Scalability, and Cost.

Efficiency: An identified user concern is how the user can seamlessly use all of these devices and securely share personalized data across them. For example, assume that a user wants to share information about an adjustable device, such as its state, what program it is running, etc. As such, a circle of trust provides a system in which a primary owner of content can share content (e.g., information about a particular medical device) with other devices that are within a circle of trust (see FIG. 2), where in various embodiments of the present invention the other devices are of device types that are the different from the adjustable device.

Security: An identified user concern is how the user can seamlessly secure and protect not only user data (e.g., data contained within a pacemaker), but also user identity. Furthermore, there is a growing number of mandates/regulations in various industries that mandate how information must be protected from being accessed by unauthorized persons (e.g., the United States Health Insurance Portability and Accountability Act of 1996—"HIPPA"). Often such security requires endpoint solutions/agents/policies etc. not only at the endpoint of the holder of the information, but also at the endpoint of the requester of the information, which is time consuming and ineffective in securing the system.

Scalability: An identified user concern is how the user and/or the user's enterprise can maintain a fleet of devices, including maintaining current software licenses for software running on such devices, reconciling different operating systems and applications on the devices, etc.

Cost: An identified user concern is keeping down costs, including the costs associated with the Efficiency, Security, and Scalability issues just discussed (e.g., reducing and/or keeping personal/business Information Technology (IT) costs under control, while still minimizing asset risks).

In order to address these issues, one or more embodiments of the present invention provide a supervisory computer solution.

Figure 2:
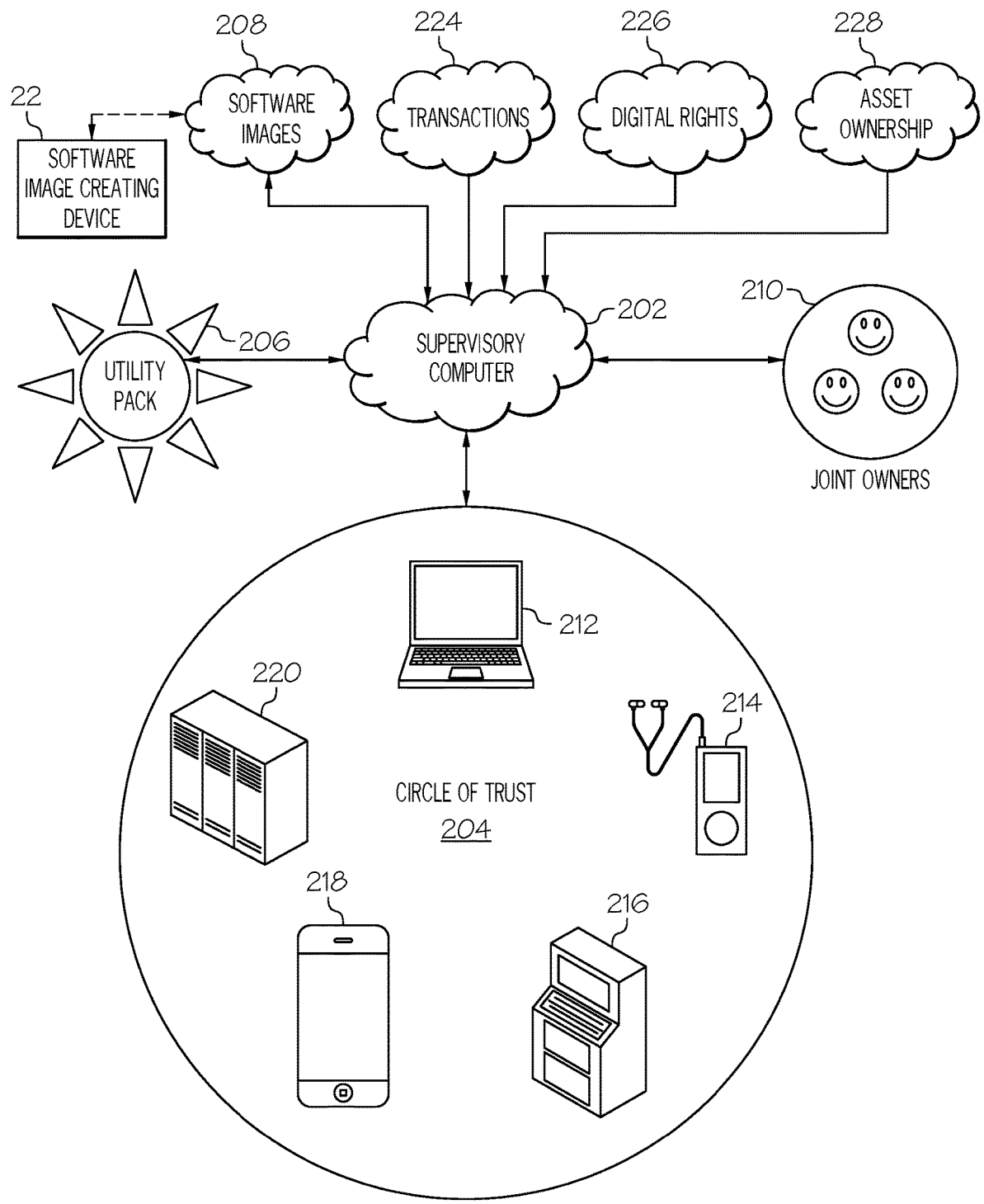
FIG. 2 depicts exemplary components of one or more embodiments of the present invention.

With reference now to FIG. 2, an overview of the use of a supervisory computer in an exemplary embodiment of the present invention is presented.

As shown in FIG. 2, a supervisory computer 202 supports a circle of trust 204 by exchanging information from a utility pack 206, software images 208, and identities of joint owners 210 with the circle of trust 204.

Supervisory computer 202 is defined and described herein as 1) a "Container" for utilities (e.g., including a portable operating system) located in utility pack 206 and software images (e.g., text documents, photos, etc.) from software images 208; 2) resides on a machine (i.e., a physical computer or a virtual machine, which is a software emulation of a hardware computer that runs on one or more physical computers and is able to emulate the functionality of a physical computer system); 3) is portable in such a way that it can manage software images that are stored and played on any device from a Set of Trusted Devices (described herein and depicted in FIG. 2 as a circle of trust 204) that are used exclusively by joint owners 210; and 4) uses the Set of Trusted Devices as a blockchain mechanism (i.e., the Set of Trusted Devices are peers in a blockchain environment) that enables secure sharing of the utilities and software images among the devices in the Set of Trusted Devices.

Figure 3:
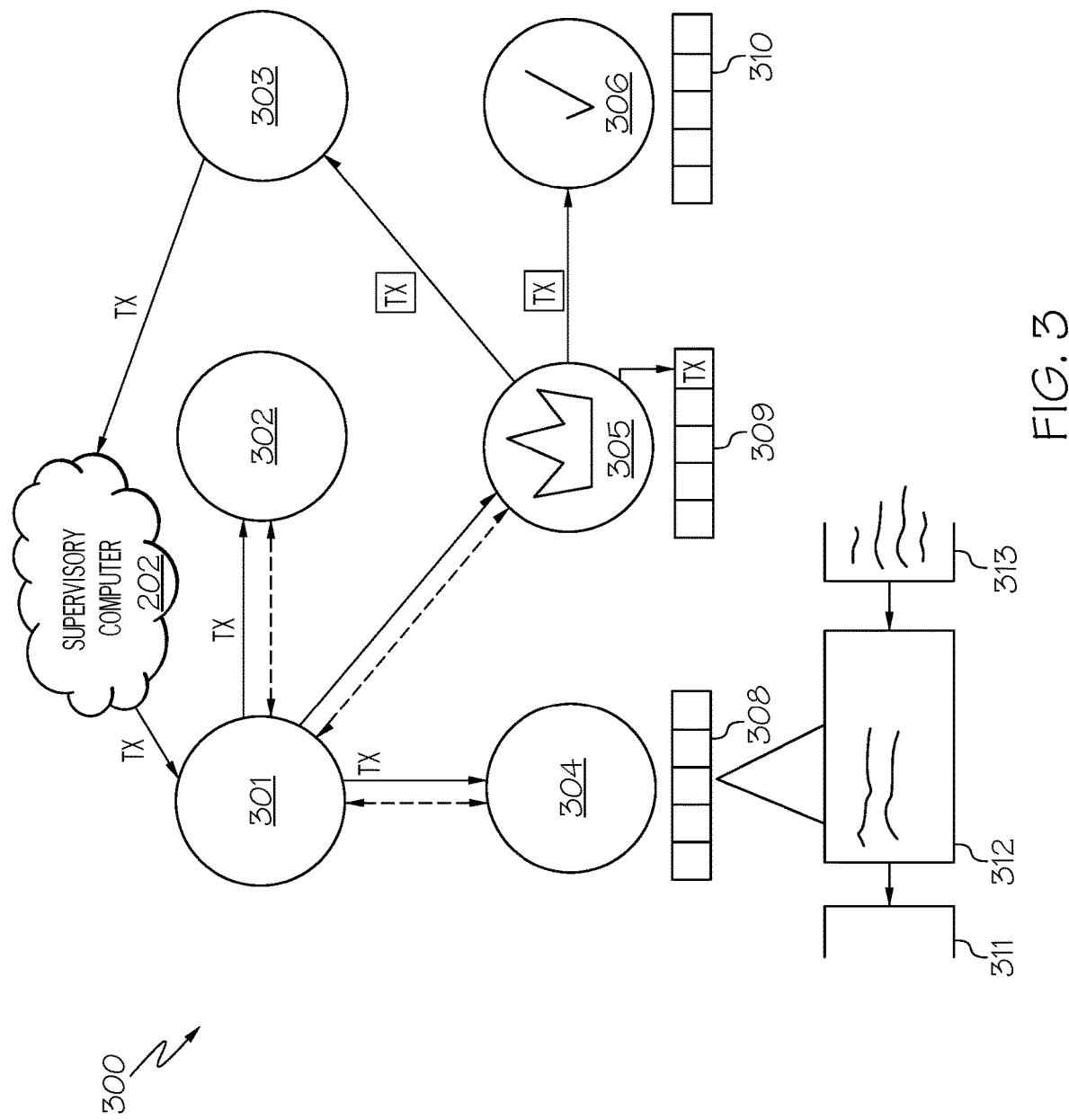
FIG. 3 illustrates an exemplary blockchain architecture as used in one or more embodiments of the present invention.

As used herein, the terms "blockchain mechanism" and "blockchain environment" are used interchangeably to describe a network of hardware devices that support blockchain processing, including but not limited to those devices depicted as blockchain networked set of trusted devices 104 shown in FIG. 1 and/or devices shown within circle of trust 204 in FIG. 2 and/or computers 301-306 shown in FIG. 3.

For purposes of illustration regarding how a supervisory computer provides Efficiency, Security, Scalability, and Cost savings to a user, consider now the following features of supervisory computer 202.

Efficiency—How does a user and/or enterprise seamlessly use all of their devices (e.g., the laptop 212, communicatively connected adjustable device 214 (e.g., a medical device such as a pacemaker), "smart" appliance 216, cell phone 218, and server 220) and share personalized data across them?

Whether it be for business or personal usage, supervisory computer 202 permits the end-user to have a consistent platform (provided by the portable OS, access to the software images 208, etc. from the supervisory computer 202) across all of his/her devices. With this standardization, the end-user has constant access to family photos or reports or other software images (i.e., digital files such as photo files, text files, video files, data files, application files, etc.) across all of their personal and/or business devices without having to be continuously hampered by cloud shares or network transfers. This access creates greater efficiency, labor reductions and reduced complexity by eliminating the requirement for the end-user to know various OS types to conduct business/personal tasks, and to always poll a cloud system whenever a software image is needed.

Security—How does a user and/or enterprise seamlessly secure and protect his/her/its identity and data, and still remain compliant with the growing number of mandates in the industry?

With a prior art standardized solution, the security needs are met mainly in platform infrastructure. With supervisory computer 202 and storage of software images 208 (e.g., medical data from the adjustable device 214) in a cloud, however, the endpoint is no longer at-risk due to a potential lack of storage/disk space. That is, using the blockchain protocol described herein, an attacker is unable to access a software image since that attacker will not also have other information in a blockchain ledger such as an identifier of the supervisory computer 202, the names of the joint owners 210, etc. Cloud security and use of the supervisory computer 202 thus allows data to be centralized such that the data does not need to leave databases (within the cloud of software images 208) as frequently, since it is virtualized/shared among the devices shown within the circle of trust 204 when required from the end-user.

Scalability—How can the user/enterprise maintain its fleet of devices, manage licensing, and unify his/her/its digital footprint?

Scalability becomes less of a concern as provisioning, Identity and Access Management (IAM) secondary controls, and other back-end processes associated with endpoints and correlating accesses are reduced. Thus, there is greater control over privileged access as the access is unified in a single supervisory computer profile.

Licensing compliance/management overhead is reduced as 1 End-User=1 License across all the various devices within the circle of trust 204.

In one or more embodiments of the present invention, each supervisory computer instance is permitted to have various profiles assigned to it.

Cost—How does the user/enterprise reduce or keep his/her/its personal Information Technology (IT) and/or business IT costs under control, while minimizing his/her/its asset risks?

First, there is a reduction in licensing costs, since 1 OS=1 License. That is, since the supervisory computer 202 provides a mobile OS that is used on all of the devices within the circle of trust 204, then only one OS license (for that portable OS) is required.

Second, a cloud solution centralizes and reduces much of the security and compliance costs.

Third, there is an overall reduction in hardware costs, maintenance, patching, policy maintenance, scanning/monitoring etc., since one overarching security solution applies across all of the devices (e.g., within the circle of trust 204) that are assigned to the supervisory computer 202.

Fourth, there are labor/complexity reductions. This reduction is on the end-user side and also that of the OS procurement and Mass Storage Service (MSS) providers.

Furthermore, with a supervisory computer, there is more consistency and opportunity to capture the end-user's habits using Behavior Analytics/Data Analytics.

Returning now to FIG. 2, utility pack 206 includes utilities (software that maintains and manages supervisory computer 202) as well as metadata related to the software images 208, such as their address/location (e.g., an Internet Protocol—IP address) on a cloud, universal resource locator (URL) addresses, etc. That is, utility pack 206 includes instructions for configuring and deploying supervisory computer 202, as well as how to locate the software images 208.

Software images 208 not only include data files such as music files, photo files, text files, etc., but also information about versions of the files, digital rights (e.g., copyright information) about the files, transaction histories for the files, the author of the files, etc. That is, software images 208 not only include any type of digital file (text, video, numeric data, photographs, etc.), but also include intellectual property information (e.g., regarding copyright status of the files, whether the files are proprietary, etc.). Software images 208 also includes a history of who/what has accessed the digital files, which device within the circle of trust 204 has been designated as the host peer in the blockchain environment created by the devices within the circle of trust 204, when the digital files were last updated, the version number of the digital files, etc.

Joint owners 210 define/identify the authorized joint owners of circle of trust 204. That is, joint owners 210 identify a particular person, enterprise, etc. that is authorized to use a particular device from the circle of trust 204 and to share software images with other devices in the circle of trust 204.

In one or more embodiments, the present invention utilizes the devices within the circle of trust 204 as peer devices in a blockchain environment. That is, devices 212-220 shown in FIG. 2 function as peers in a blockchain environment, such that they not only are able to acquire software images 208 from the supervisory computer 202 and share software images to and from other devices within the circle of trust 204, but also use blockchain technology to protect the software images 208 from being divulged to an unauthorized party.

In an embodiment of the present invention, some or all of the software images 208 are initially created by one or more of the devices within circle of trust 204.

In an embodiment of the present invention, some or all of the software images 208 are initially created by a software image creating device 222, which in an embodiment of the present invention is a content supplier (e.g., a database server).

Also in communication with supervisory computer 202 is a record of transactions 224, which describes content that has been created by and/or shared among devices within the circle of trust 204.

Also in communication within supervisory computer 202 is a record of digital rights 226, which describes digital rights (e.g., copyrights) of content that is created using one or more of the devices within the circle of trust 204.

Also in communication with supervisory computer 202 is a record of asset ownership 228 of devices within the circle of trust 204. This record includes identities of particular users who own (or are authorized to use) each of the devices in the circle of trust 204, in order to verify that the particular user is authorized to communicate with the supervisory computer 202, provide content to the circle of trust 204, etc. The records of asset ownership 228 take on the form of legal documents (e.g., recorded registration of adjustable device 214), a lookup table of authorized users/owners of laptop 212, etc.

In an embodiment of the present invention, the circle of trust 204 provides a blockchain environment that provides a secure environment for implementing the present invention. That is, one or more embodiments provide a secure environment in which content can be shared among devices in the circle of trust 204, which are physical devices. In one or more such embodiments, the devices in the circle of trust 204 function as peers in a blockchain.

Exemplary blockchain environments, which are provided using the devices within the circle of trust 204 in accordance with one or more preferred embodiments of the present invention, are described now in FIGS. 3-7.

With reference now to FIG. 3, an illustration of an exemplary blockchain environment 300 as used in one or more embodiments of the present invention is presented. As shown in FIG. 3, computers 301, 302, 303, 304, 305, and 306 (e.g., blockchain networked set of trusted devices 104 shown in FIG. 1, also represented in FIG. 2 as elements 212-220 within the circle of trust 204) represent an exemplary peer-to-peer network of devices used to support a peer blockchain environment (in which more or fewer computers/machines form the peer-to-peer network of devices). Each of the computers 301, 302, 303, 304, 305 and 306 (which are telecommunication devices, portable computers, servers, smart appliances, smart medical devices, cell phones, etc.) in the peer-to-peer network have a same copy of data (e.g., data that represents transaction events), as held in ledgers stored within the depicted blockchains 308, 309, 310 that are associated with respective computers 304, 305, 306.

As shown in FIG. 3, computer 303 (i.e., one of the devices within the circle of trust 204 shown in FIG. 2) sends a transaction Tx (e.g., a new request for a digital file from software images 208, a request to add or delete a device from the circle of trust 204, etc.) to supervisory computer 202. supervisory computer 202 then sends the transaction Tx to another device within the circle of trust 204, which is a blockchain environment peer that is depicted as computer 301. Computer 301 then sends the transaction Tx to ledgers known as the depicted blockchains 308, 309, 310 that are associated with other peers, including the depicted computers 302, 304, 305.

Blocks within exemplary blockchain 308 are depicted as block 311, block 312, and block 313. Block 313 is depicted as a newest entry into a ledger held in blockchain 308, and includes not only the newest transactions but also a hash of the data from the older block 312, which includes a hash of the even older block 311. Thus, older blocks are made even more secure each time a new block is created, due to the hashing operations.

With reference now to FIG. 4, an exemplary blockchain ledger 400 within blockchain 308 as utilized in one or more embodiments of the present invention is depicted.

In one or more embodiments of the present invention, blockchain ledger 400 includes an identifier of the supervisory computer that supports the circle of trust 204, as shown in block 402. For example, in one or more embodiments of the present invention block 402 includes an internet protocol (IP) address, a uniform resource locator (URL), etc. of the supervisory computer. This information is used by peers in the circle of trust 204 to locate software images 208, retrieve a portable OS (that can run on any of the devices in the circle of trust 204), etc.

In one or more embodiments of the present invention, blockchain ledger 400 also includes identifiers for each device within the circle of trust 204, as shown in block 404. In various embodiments of the present invention, these identifiers are in the form of IP addresses, media access protocol (MAC) addresses, universally unique identifiers (UUIDs), etc. of each device, or alternatively are in the form of a pseudonym (e.g., "Bob's pacemaker"), for which the IP, MAC address, UUID, etc. can be located using a lookup table that is either within block 404 or is located within utility pack 206 shown in FIG. 2. This information allows each device within the circle of trust 204 to know which devices are its blockchain peers.

In one or more embodiments of the present invention, blockchain ledger 400 also includes the identities of the persons or other entities (e.g., enterprises) that own or are otherwise associated with each of the devices within the circle of trust 204, as shown in block 406. This allows the devices within the circle of trust 204 to recognize an authorized person who creates a transaction for the circle of trust 204.

In one or more embodiments of the present invention, blockchain ledger 400 also includes a copy of one or more software images that are shared among the devices within the circle of trust 204, as shown in block 408. In one or more embodiments, these software images originate in the cloud of software images 208 shown in FIG. 2, but are not blockchain-protected by the blockchain that is found within the blockchain environment that is provided by the supervisory computer 202 and the circle of trust 204. This allows the members of the circle of trust 204 to maintain a copy of the software images (if space is available), such that there is no security risk from going "outside of the circle of trust 204" in order to retrieve the software image(s).

In one or more embodiments of the present invention, blockchain ledger 400 also includes software image metadata, as shown in block 410. This software image metadata includes information from the software images 208 such as copyright status, usage history, pseudonyms (e.g., "Bob's pacemaker"), etc. of the software image(s) shown in block 408. This allows members of the circle of trust 204 to further recognize and manage the software image(s).

In one or more embodiments of the present invention, blockchain ledger 400 also includes a copy of the current state of an adjustable device, as shown in block 412. That is, an adjustable device is known by the blockchain to be in a certain state (e.g., has been programmed to meet certain parameters, etc.). Only the information in block 412 is to be trusted as accurate for that adjustable device, such that any variation from the information in block 412 is deemed to be invalid or unauthorized. Thus, the blockchain is able to maintain a record of authorized changes to the adjustable device's current state, which must be comported with when any changes are made to the adjustable device.

In one or more embodiments of the present invention, blockchain ledger 400 also includes a description of the transaction shown in FIG. 4 (see block 414), as provided by transactions 224 shown in FIG. 2. That is, assume that a member of the circle of trust 204 requests that a new software image 208 be promulgated among the devices within the circle of trust 204, or that a new member be added to the circle of trust 204, or that an existing member be removed from the circle of trust 204, or that a particular member of the circle of trust 204 be barred from accessing a certain software image that is being shared by other members of the circle of trust 204, etc. Within block 414 is either a description of the transaction (which can be retrieved using a lookup table), or executable code capable of performing the operation described in the transaction is stored within block 414 for immediate access by members of the circle of trust 204. This information is used by peers/devices within the circle of trust 204 to ensure that any newly received version of ledger 400 matches known activities (based on prior versions of the ledger 400).

In one or more embodiments of the present invention, blockchain ledger 400 also includes a copy of a legal document (see block 416), which describes rights to content that is to be shared among one or more of the devices within the circle of trust 204 depicted in FIG. 2.

In one or more embodiments of the present invention, blockchain ledger 400 also includes a description of digital rights for content (see block 418), which describes information from the digital rights 226 depicted in FIG. 2.

In one or more embodiments of the present invention, blockchain ledger 400 also includes a copy of asset ownership (see block 420), which is a copy of a document from asset ownership 228 that describes legal ownership of one or more of the devices within the circle of trust 204 depicted in FIG. 2.

Returning now to FIG. 3, computer 305 (e.g., laptop 212 shown in FIG. 2) has been designated as a leader peer according to a consensus model of the peer-to-peer network. In order to be designated as the leader peer, computer 305 has to be the first to "guess" what the data (i.e., the ledger) in Tx is. That is, computer 301 encrypted Tx with a prior one-way encryption algorithm (e.g., Secure Hash Algorithm 2—"SHA-2"). Since this is a one-way encryption algorithm, there is no way to know what was used as the input by simply reverse-engineering the encryption. However, blockchain protocols require that the leading bits in the encrypted (hashed) data follow a certain pattern, such as eight leading zeros followed by other bits (e.g., "00000000xxxxxxxxxxxx"). Thus, computer 305 simply used brute force to input many combinations of data into the SHA-2 algorithm until an output of "00000000xxxxxxxxxxxx" is achieved. Since the first eight bits were correct ("00000000"), then there is an assumption that the other bits ("xxxxxxxxxxxx") are also correct, since the odds of getting "00000000" correct but not getting "xxxxxxxxxxxx" are extremely small. Note that while computer 305 is working on this problem (of guessing what the input data to the SHA-2 algorithm by computer 301 is), other computers such as computers 301-304 and 306 are also working on the problem.

Assume now that computer 305 won the "race" to decrypt Tx before computers 301-304 and 306. Thus, computer 305 will send the data ("00000000xxxxxxxxxxxx") in a newly-encrypted form (using a key provided by computer 301) to one or more of computers 301-304 and 306. One or more of computers 301-304 and 306 will then check computer 305's work. Once a predefined quantity of peer computers from computers 301-304 and 306 (in a preferred embodiment, all of the peer computers 301-304 and 306) agree that the decrypted value of Tx is correct, then computer 305 will be designated as the leader peer for Tx. That is, the nodes/computers that receive the new block/transaction (Tx) then attempt to validate the new block/transaction. If enough (i.e., some predefined quantity/percentage) of the nodes/computers validate the new block/transaction, then the new block/transaction is deemed valid for the entire peer-to-peer network of computers 301-306 and is added to the blockchains (including the depicted blockchains 308, 309, 310) associated with all of the nodes/peers/computers 301-306.

As such, the leader peer (computer 305) organizes all transactions from the nodes/peers/computers/telecommunication devices 301-306, and then shares new blocks/transactions (Tx) with other nodes (e.g., computers 303, 306) as depicted.

In one or more embodiments of the present invention, the blockchains (including the depicted blockchains 308, 309, 310) are "anchored" to a particular user by adding to the block/transaction information such as that shown in FIG. 4.

Figure 5:
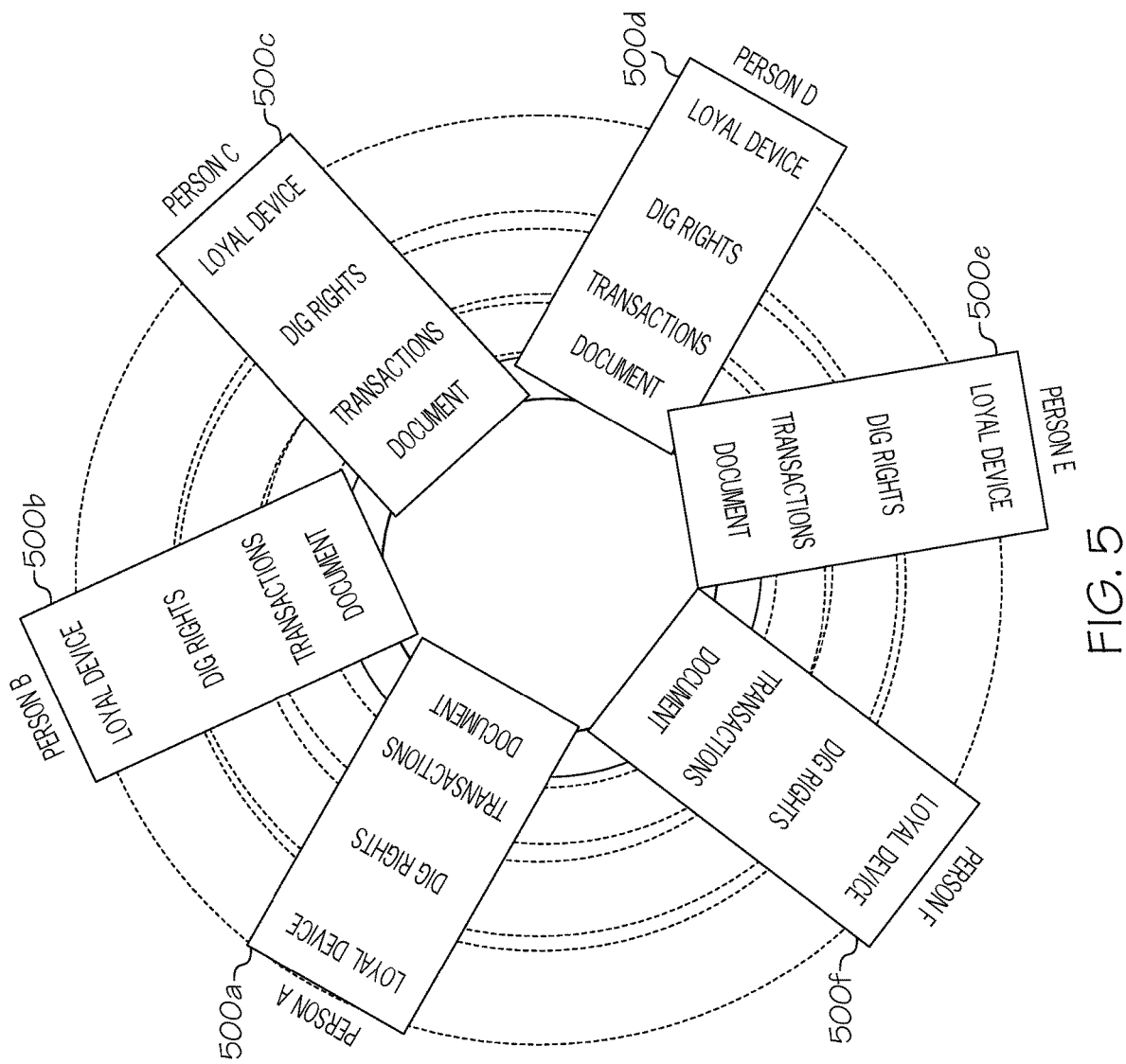
FIG. 5 illustrates multiple parties, each of which has his/her/its own copy of a blockchain, according to one or more embodiments of the present invention.

As shown in FIG. 5, in an embodiment, each person using one of the devices within circle of trust 204 has his/her own block that is equivalent to block 400 shown in FIG. 4. That is, each person has a unique block that is part of the blockchain environment. Thus, Person A has his/her own block 500a; Person B has his/her own block 500b; Person C has his/her own block 500c; Person D has his/her own block 500d; Person E has his/her own block 500e; Person F has his/her own block 500f; etc.

Figure 6:
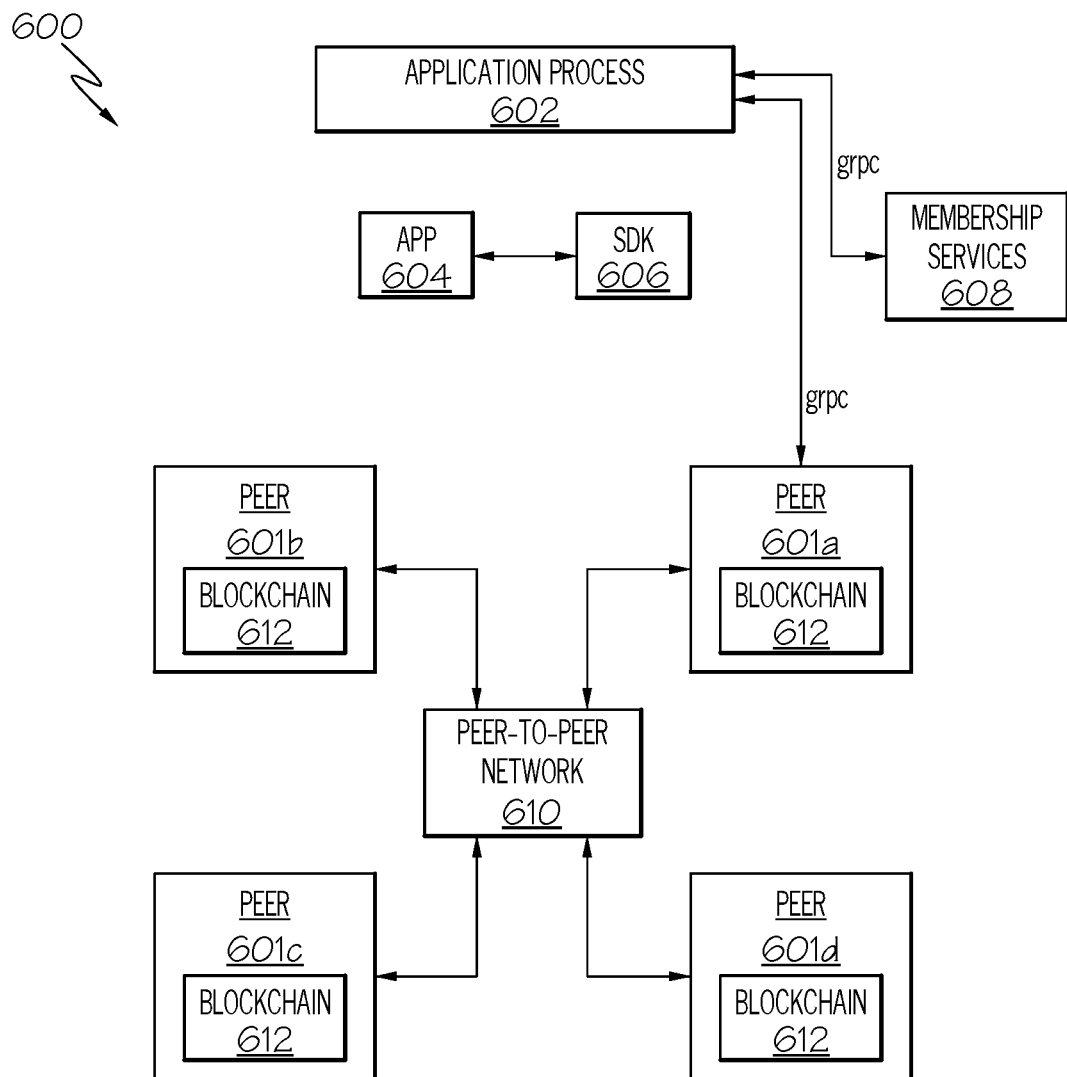
FIG. 6 depicts additional detail of an exemplary blockchain topology as used in one or more embodiments of the present invention.
Figure 7:
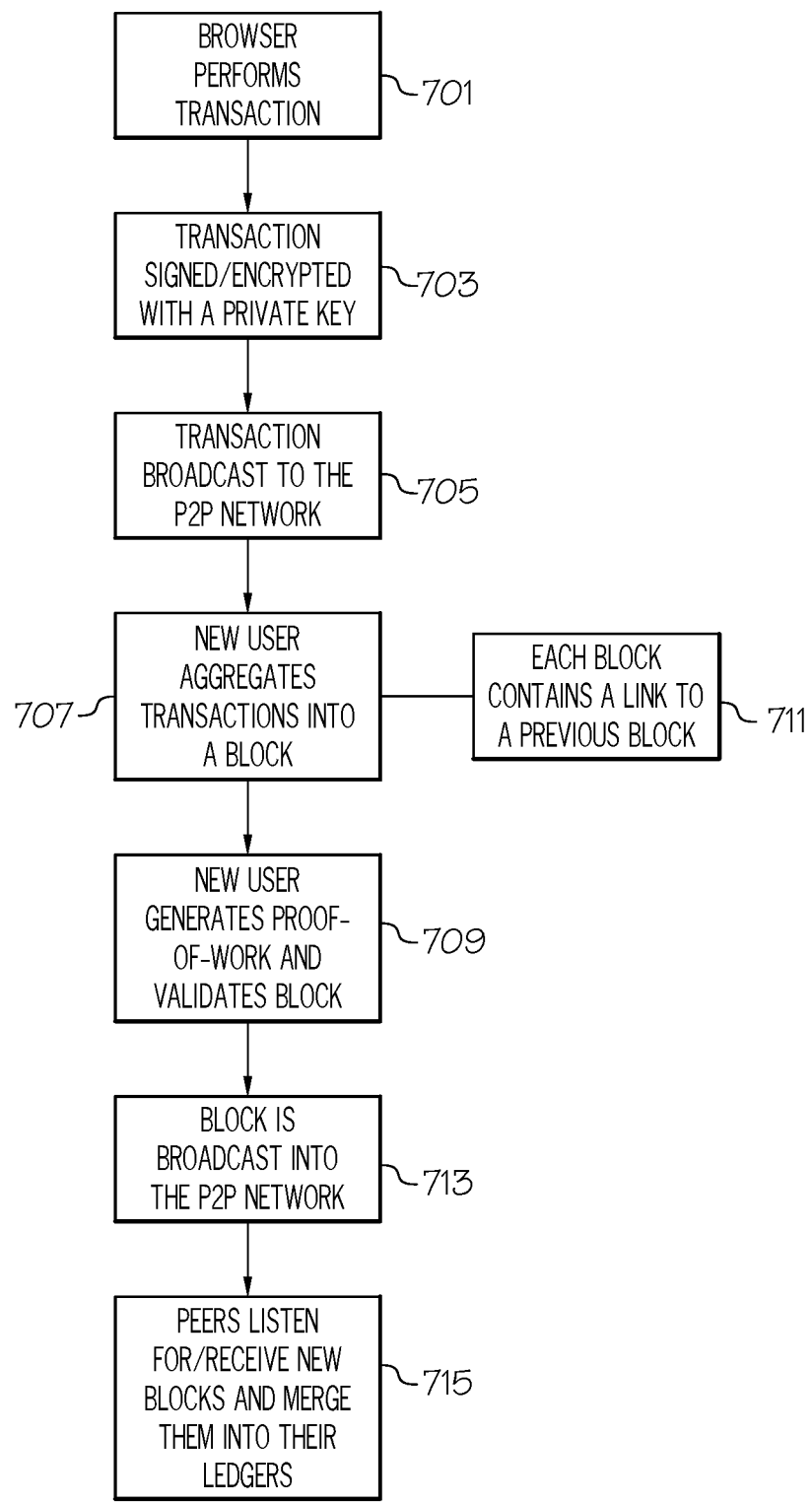
FIG. 7 illustrates a high-level use of a blockchain in accordance with one or more embodiments of the present invention.

With reference now to FIGS. 6-7, additional detail of a blockchain and its operation as used in one or more embodiments of the present invention is presented.

In one or more embodiments of the present invention, a blockchain fabric, such as blockchain fabric 600 depicted in FIG. 6, is used to provide the infrastructure (e.g. execution of the chaincodes) and services (e.g., Membership services such as Identity management) for securely and transparently storing, tracking and managing transactions on a "single point of truth". The blockchain fabric 600 maintains a verifiable record (of the single point of truth) of every single transaction ever made within the system. Once data are entered onto the blockchain, they can never be erased (immutability) or changed. That is, a change to a record would be regarded as issuing/introducing a new transaction. Prohibition of such thus ensures auditability and verifiability of data.

The blockchain fabric 600 (also known as the "blockchain system", "open blockchain" or "hyperledger fabric") is based on a distributed database of records of all transactions or digital events that have been executed and shared among participating parties. An individual transaction in the blockchain is validated or verified through a consensus mechanism incorporating a majority of the participants in the system. This allows the participating entities to know for certain that a digital event happened by creating an irrefutable record in a permissioned public ledger.

When a transaction is executed, its corresponding chaincode is executed by several validating peers of the system. For example, as shown in FIG. 6, peers 601a-601d (i.e., other computers, servers, etc.) establish the validity of the transaction parameters and, once they reach consensus, a new block is generated and appended onto the blockchain network. That is, an application process 602 running on a client (e.g., an application on supervisory computer 202 shown in FIG. 3) executes an application such as the depicted App 604, causing a software development kit (SDK) 606 to communicate using general remote procedure calls (grpc) to membership services 608 that support the peer-to-peer network 610 that supports the blockchain 612 using the peers 601a-601d.

Exemplary operation of the open blockchain fabric 600 shown in FIG. 6 is presented in FIG. 7. As described in step 701, a browser or other device (e.g., supervisory computer 202 shown in FIG. 3) performs a transaction (e.g., to retrieve updated data shared among devices within the circle of trust 204). As shown in step 703, the client (e.g., supervisory computer 202) signs and encrypts the transaction with a private key, such as Secure Hash Algorithm (SHA)-2. This Secure Hash Algorithm (SHA-2)-encrypted transaction is then broadcast to the peer-to-peer network 610, as described in step 705. A new user (e.g., peer 601c) aggregates the transaction(s) into blockchain 612, as shown in step 707. As shown in block 711, each block contains a link to a previous block. The newly-revised blockchain 612 is validated by one or more of the other peers in peers 601a-601d (step 709), and is then broadcast to the peers 601a-601b and peer 601d, as described in step 713. These peers 601a-601b and peer 601d listen for and receive the new blocks and merge them into their copies of blockchain 612 (step 715).

Thus, the open blockchain fabric 600 shown in FIG. 6 is a blockchain deployment topology that provides a distributed ledger, which persists and manages digital events, called transactions, shared among several participants, each having a stake in these events. The ledger can only be updated by consensus among the participants. Furthermore, once transactions are recorded, they can never be altered (they are immutable). Every such recorded transaction is cryptographically verifiable with proof of agreement from the participants, thus providing a robust provenance mechanism tracking their origination.

As such, a blockchain fabric uses a distributed network to maintain a digital ledger of events, thus providing excellent security for the digital ledger, since the blockchain stored in each peer is dependent upon earlier blocks, which provide encryption data for subsequent blocks in the blockchain.

That is, the open blockchain fabric 600 shown in FIG. 6 provides a decentralized system in which every node in a decentralized system has a copy of the blockchain. This avoids the need to have a centralized database managed by a trusted third party. Transactions are broadcast to the network using software applications. Network nodes can validate transactions, add them to their copy and then broadcast these additions to other nodes. However, as noted above, the blockchain is nonetheless highly secure, since each new block is protected (e.g., encrypted) based on one or more previous blocks.

Figure 8:
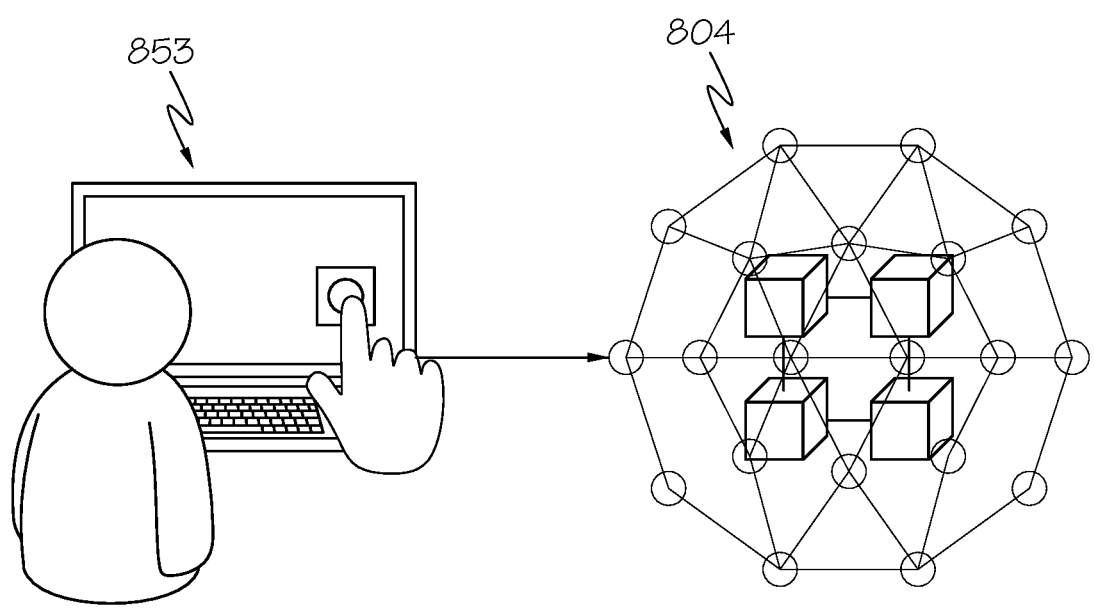
FIG. 8 depicts a high-level overview of one or more embodiments of the present invention.

With reference now to FIG. 8, assume now that a user (e.g., a person who wishes to reprogram a pacemaker) or the device itself, as shown as adjustable device 853 (analogous to adjustable device 153 shown in FIG. 1), requests authorization for and/or information needed to reprogram the pacemaker. This reprogramming is referred to as a "transaction". In order to reprogram the device 853, the user needs two items: authorization and instructions, both of which are provided by the circle of trust 804 (analogous to the circle of trust 204 shown in FIG. 2). That is, the circle of trust 804 functions as a set of blockchain devices (analogous to blockchain environment 300 shown in FIG. 3), which manage blockchain ledgers, such as the blockchain ledger 400 shown in FIG. 4. These blockchain ledgers include not only an authorization code that allows the user to modify the adjustable device 853, but also include a current authorized programmed state of the adjustable device 853. (See block 412 in the blockchain ledger 400 shown in FIG. 4.) This current authorized programmed state of the adjustable device 853 is required to make any changes to the programmed state of the adjustable device 853. That is, if the programming change were to read "Change the sensitivity level of the sensor lead from 0.5 mV to 0.4 mV", but the current sensitivity of the sensor lead is currently 0.3 mV, then the command would fail, since it does not comport with the current state of that pacemaker as described in the blockchain ledger for that pacemaker.

In addition, the blockchain ledger contains an authorization code, which allows the programming device to reprogram the adjustable device (e.g., the pacemaker).

FIG. 9 illustrates additional detail of one or more embodiments of the present invention.

Assume now, for purposes of illustration of an exemplary embodiment of the present invention, that the patient pacemaker 953 shown in FIG. 9 (analogous to adjustable device 853 shown in FIG. 8) can be modified, reprogrammed, etc. to adjust the sensitivity of sensors in the patient pacemaker 953 that monitor the patient's heart, to adjust the frequency of stimuli sent from the patient pacemaker 953 to the patient's heart (i.e., in order to make the patient's heart beat at a certain number of beats per minute), to adjust the type of data about the patient's heart that is stored in the patient pacemaker 953, to define what types of devices are capable of and/or are authorized to retrieve stored data from the patient pacemaker 953, to define what types of devices are capable of and/or are authorized to reprogram the patient pacemaker 953, etc.

A circle of trust 904 (analogous to the circle of trust 804 shown in FIG. 8) is a collection of devices that 1) are capable of adjusting the patient pacemaker 953; 2) function together as a blockchain environment that controls the patient pacemaker 953; and/or 3) includes the patient pacemaker 953 in a first embodiment but excludes the patient pacemaker 953 in a second embodiment.

Thus, assume for purposes of illustration of one or more embodiments of the present invention, that the circle of trust 904 includes the patient pacemaker 953, as depicted in FIG. 9. As shown in FIG. 9, other devices within the circle of trust 904 include patient devices 901, wand/reader 903, hospital issued home monitoring device 905, in hospital device programmer 907, and doctor's laptop 909.

Patient devices 901 are devices such as Internet of Things (IoT) wearable devices such as smart watches, smart phones, etc. In one or more embodiments of the present invention, patient devices 901 are able to adjust/reprogram/modify the patient pacemaker 953 by utilizing the circle of trust 904 to control/manage the actual adjustment/reprogramming/modification of the patient pacemaker 953, as described herein.

In one or more embodiments of the present invention, Wand/reader 903 is able to adjust/reprogram/modify the patient pacemaker 953 by utilizing the circle of trust 904 to control/manage the actual adjustment/reprogramming/modification of the patient pacemaker 953, as described herein.

In one or more embodiments of the present invention, hospital issued home monitoring device 905 is able to adjust/reprogram/modify the patient pacemaker 953 by utilizing the circle of trust 904 to control/manage the actual adjustment/reprogramming/modification of the patient pacemaker 953, as described herein.

In one or more embodiments of the present invention, hospital device programmer 907 is able to adjust/reprogram/modify the patient pacemaker 953 by utilizing the circle of trust 904 to control/manage the actual adjustment/reprogramming/modification of the patient pacemaker 953, as described herein.

In one or more embodiments of the present invention, doctor's laptop 909 is able to adjust/reprogram/modify the patient pacemaker 953 by utilizing the circle of trust 904 to control/manage the actual adjustment/reprogramming/modification of the patient pacemaker 953, as described herein.

Beyond being devices that are all able to modify and/or monitor the patient pacemaker 953, the devices shown as the circle of trust 904 also include processing logic that allows them to be nodes in the blockchain environment 300 shown in FIG. 3. In an embodiment of the present invention, only devices that are able to modify/monitor the adjustable device (e.g., patient pacemaker 953) are allowed to be part of the circle of trust 904, thus preserving the integrity of the circle of trust 904 by limiting membership to only those devices that have this ability and a direct relationship with the adjustable device.

As shown by exemplary biometric marker 911 in FIG. 9, biometric authentication is used by one or more devices in the circle of trust 904. That is, before a device (e.g., the hospital issued home monitoring device 905, the in hospital device programmer 907, the doctor's laptop 909) is allowed to send a transaction to another device in the circle of trust 904 (i.e., the blockchain environment 300 shown in FIG. 3), a user of the device must first provide biomarker authentication (e.g., a fingerprint) of his/her identity, thus providing further control over which particular devices are allowed to send/receive transactions within the blockchain environment. Control of which devices are allowed to send/receive transactions within the blockchain environment is further (or alternatively) controlled by a smart contract (which controls operations of the blockchain environment) or other operational customization (e.g., modifications to the devices in the circle of trust 904 that allows them to only accept transactions that have a field that identifies the payload in the transaction as being related to the patient pacemaker 953).

In an embodiment of the present invention, data shared across devices in the circle of trust 904 is defined in data layers within the blockchain environment to ensure data integrity, and to secure private/personal information with only those with individuals or devices with the need for such data types.

Furthermore, a firewall can prevent unauthorized devices from joining the circle of trust 904.

With reference then to FIG. 10, assume for purposes of illustration of an exemplary embodiment of the present invention that a circle of trust 1004 (i.e., a group of devices that act as a blockchain environment, as described above for circle of trust 904) is composed of four devices: wand/reader 903, hospital device programmer 907, doctor's laptop 909, and patient pacemaker 953 (depicted and described in FIG. 9). As shown in FIG. 10, each of these devices has a copy of a blockchain for the patient pacemaker 953, which includes blocks of data layers 1006. In an exemplary embodiment of the present invention, these data layers 1006 include device data 1008, performance data 1010, environmental data 1012, patient data 1014, and emergency medical services (EMS) data 1016.

Device data 1008 includes, but is not limited to, data that describes a make/model/firmware used by the patient pacemaker 953.

Performance data 1010 includes, but is not limited to, the battery life remaining, the beats per minute (BPM) that have been captured by the patient pacemaker 953, etc.

Environmental data 1012 includes, but is not limited to, a description of the circle of trust 1004 and its members, which trusted network(s) are used by the circle of trust 1004, etc.

Patient data 1014 includes, but is not limited to, patient biometrics and/or device requirements of the patient pacemaker 953 for treatment of the patient. That is, patient data 1014 includes both a biometric identification of the patient, a description of the patient's medical condition, and/or what capabilities of the patient pacemaker 953 are required in order to treat/monitor that patient's medical condition.

Emergency medical services (EMS) data 1016 includes, but is not limited to, what treatments have been provided to the patient who has the patient pacemaker 953, as well as instructions for when to automatically contact (e.g., by a signal to a monitoring device, such as the patient's smart phone) local emergency services if the patient needs medical assistance (e.g., an ambulance ride to a hospital, a remote resetting of the patient pacemaker 953, etc.). That is, the EMS data 1016 can not only call for an ambulance, but can also direct one of the patient devices 901 shown in FIG. 9 to automatically reset the patient pacemaker 953 based on a current medical state of the patient's heart (e.g., is beating too fast) and the current setting of the patient pacemaker 953 (e.g., is sending stimulation signals to the heart too rapidly).

As shown in FIG. 10, unauthorized devices, such as the depicted device 5 (unauthorized device 1018) are prevented from joining the circle of trust 1004 by a firewall 1020. For example, assume that unauthorized device 1018 is analogous to unauthorized device 118 shown in FIG. 1, and that the firewall 1020 is a combination of hardware/ports/software within the computer 101 shown in FIG. 1. As such, the computer 101 will interrogate the header of any message sent to the blockchain networked set of trusted devices 104 (i.e., the circle of trust 1004 shown in FIG. 10), and will only permit known members of that circle of trust 1004 (which does not include the unauthorized device 1018) to receive/send data from/to the circle of trust 1004.

In an embodiment of the present invention, beyond device enablement/permissions/sharing as a circle-of-trust controlled group, the data layers 1006 are broken down into "need to know" data layers/types. For example, a patient wearable device (e.g., one of the patient devices 901 shown in FIG. 9) does not need all patient data to perform its functions, so only the performance data 1010, environmental data 1012, and EMS data 1016 are accessible by the patient's wearable device (e.g., a smart watch), while the device data 1008 is not accessible to the smart watch (since the smart watch is already in near field communication with the patient pacemaker 953). Likewise, the patient data 1014 is not accessible to the smart watch, since the wearer of the smart watch already knows who he/she is.

Figure 11:
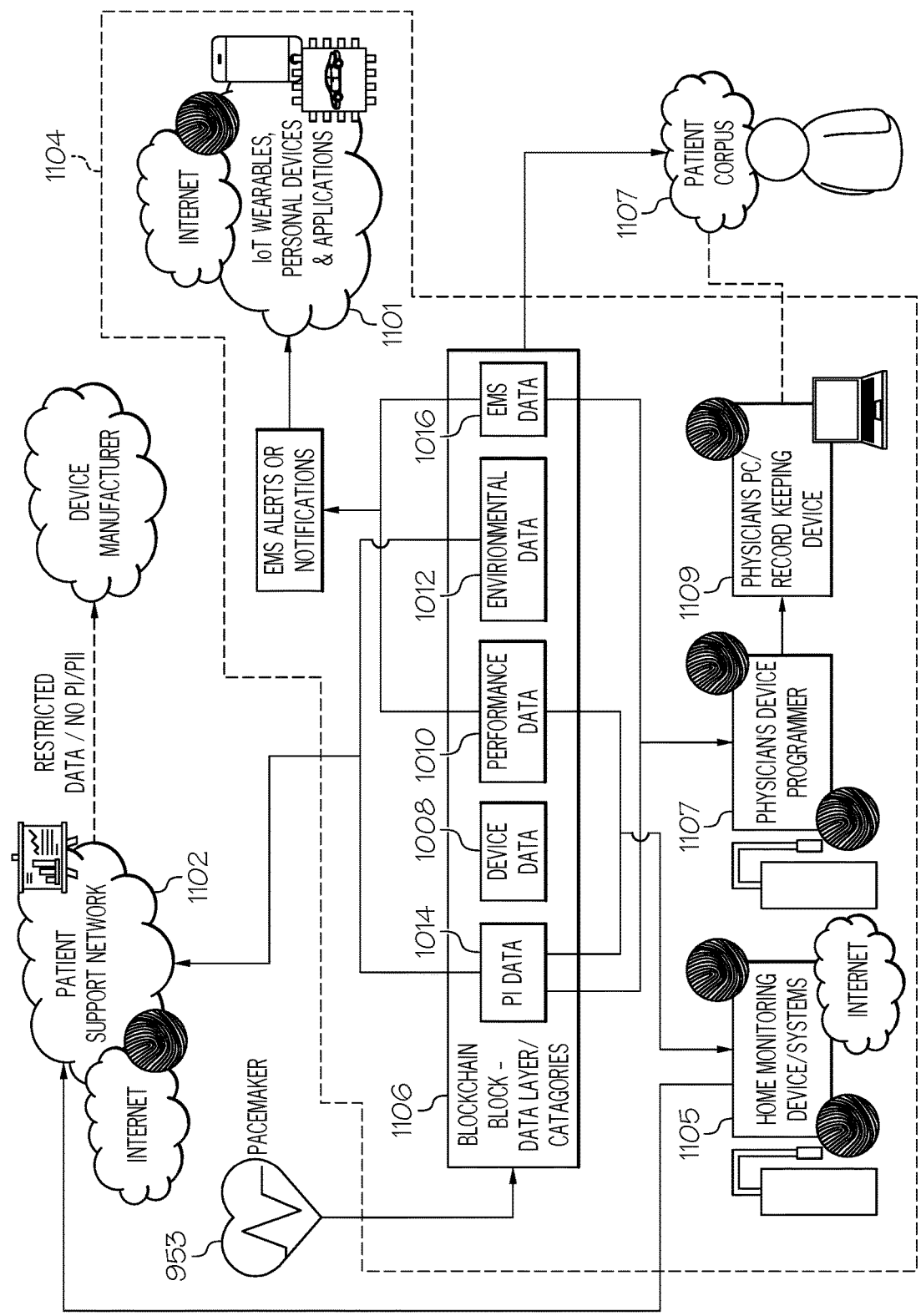
FIG. 11 illustrates additional features of one or more embodiments of the present invention.

With reference now to FIG. 11, another overview of the circle of trust 904 shown in FIG. 9 and the circle of trust 1004 shown in FIG. 10 is presented as circle of trust 1104.

As in circle of trust 904 and/or circle of trust 1004, circle of trust 1104 includes an Internet of Things (IoT) 1101 (e.g., smart phones, laptops, wearable computer devices, etc. analogous to patient devices 901 shown in FIG. 9) home monitoring device systems 1105 (analogous to hospital issued home monitoring device 905 shown in FIG. 9), a physician's device programmer 1107 (analogous to in hospital device programmer 907 shown in FIG. 9), and a physician's personal computer/record keeping device 1109 (analogous to the doctor's laptop 909 shown in FIG. 9). The patient pacemaker 953 is part of the circle of trust 1104 in an embodiment of the present invention, or is communicatively coupled to, but is not a member of, the circle of trust 1104, which controls the patient pacemaker 953.

The members of the circle of trust 1104 provide a blockchain environment, which shares the data layers 1006 shown in FIG. 10 (i.e., patient data 1014, device data 1008, performance data 1010, environmental data 1012, and EMS data 1016) as a blockchain 1106 of data.

In addition, the devices in the circle of trust 1104 are in communication with a patient support network 1102, which provides alerts and data updates (regarding the patient pacemaker 953) to health care providers. Similarly, the devices in the circle of trust 1104 are in communication with a patient corpus 1107, which provides alerts and data updates (regarding the patient pacemaker 953) to a corpus of data about the patient who is wearing the patient pacemaker 953. This corpus of data (e.g., current performance data) is thus available to the patient who is wearing the patient pacemaker 953.

Figure 12:
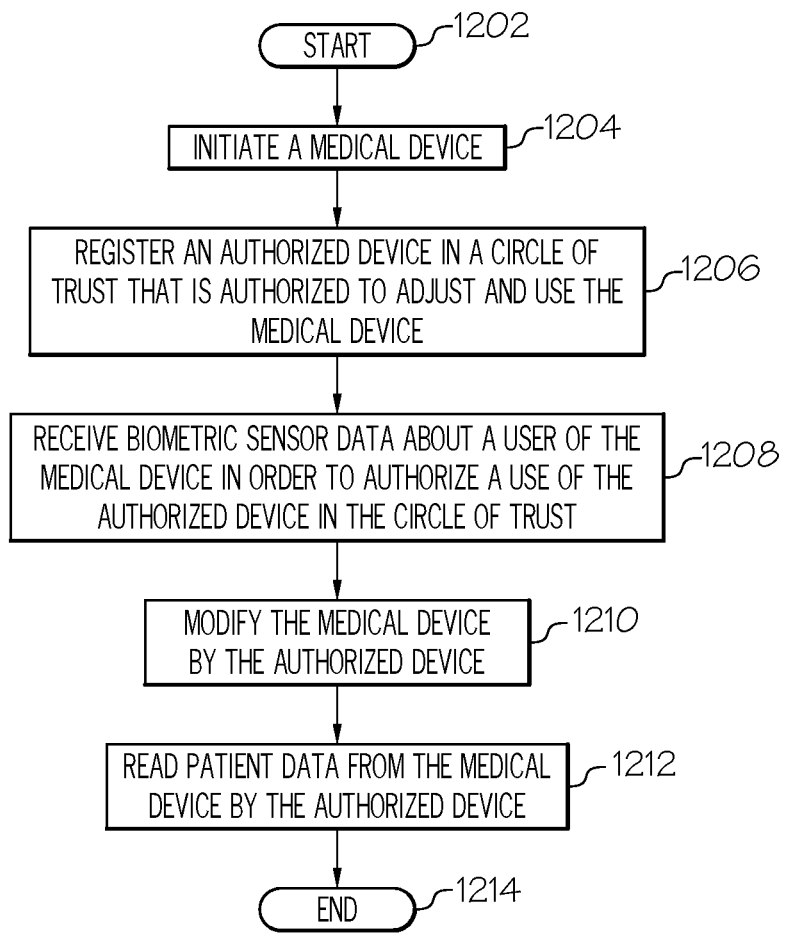
FIG. 12 depicts a flow-chart of an exemplary use case of the present invention.

An illustrative use case that describes an initiation/registration of device to start the lifecycle of devices in a circle of trust is depicted in FIG. 12.

After initiator block 1202, and upon procurement of a device (e.g., a pacemaker device), the device goes through an initiation process that includes registering the consumer (patient's) data, biometrics and authentication as consumer/owner of the information, as shown in block 1204. This data becomes the master information to which a programmer system will authenticate to in order to program the device.

As described in block 1206, additional authorized user/entities are registered. These users include, but are not limited to, a programmer system, doctor, nurse, etc. The programmer system becomes a system entity and the doctor, nurse, etc. are users. All users/entities are registered as being associated with the pacemaker device owned by the patient. The system entity becomes the only entity authorized to program the device subject to the user entity's permission and authority, which is granted at the time of registration.

As shown in block 1208, biometrics of the patients are used and authenticated at the device level in order to allow the system entity to grant these privileges to each user. In a preferred embodiment of the present invention these privileges cannot be modified at the system entity level (i.e., by the programmer device) without re-authentication and authorization by the pacemaker device. Thus, a circle of trust is established in which the pacemaker device and the owner/patient's biometrics becomes the master authentication to allow for any modifications.

As shown in block 1210, the pacemaker (medical device) is then modified. Note that any future modification required by the pacemaker via the system entity (programmer device) requires patient authentication and authorization. This also includes any patch update provided by the manufacturer. This prevents the programmer device from modifying the pacemaker device without authentication and authorization.

As shown in block 1212, patient data is read from the medical device by an authorized device. That is, the pacemaker device will store all patient information, health report data, etc. (which is preferably signatures/keys first established during registration) such that only system entities (including home/hospital devices) registered with the pacemaker device are allowed to read health data off of the pacemaker. When data is read and transferred to a programmer device, it will be obfuscated depending on the user (role) reading the data.

The flow-chart ends at terminator block 1214.

Figure 13:
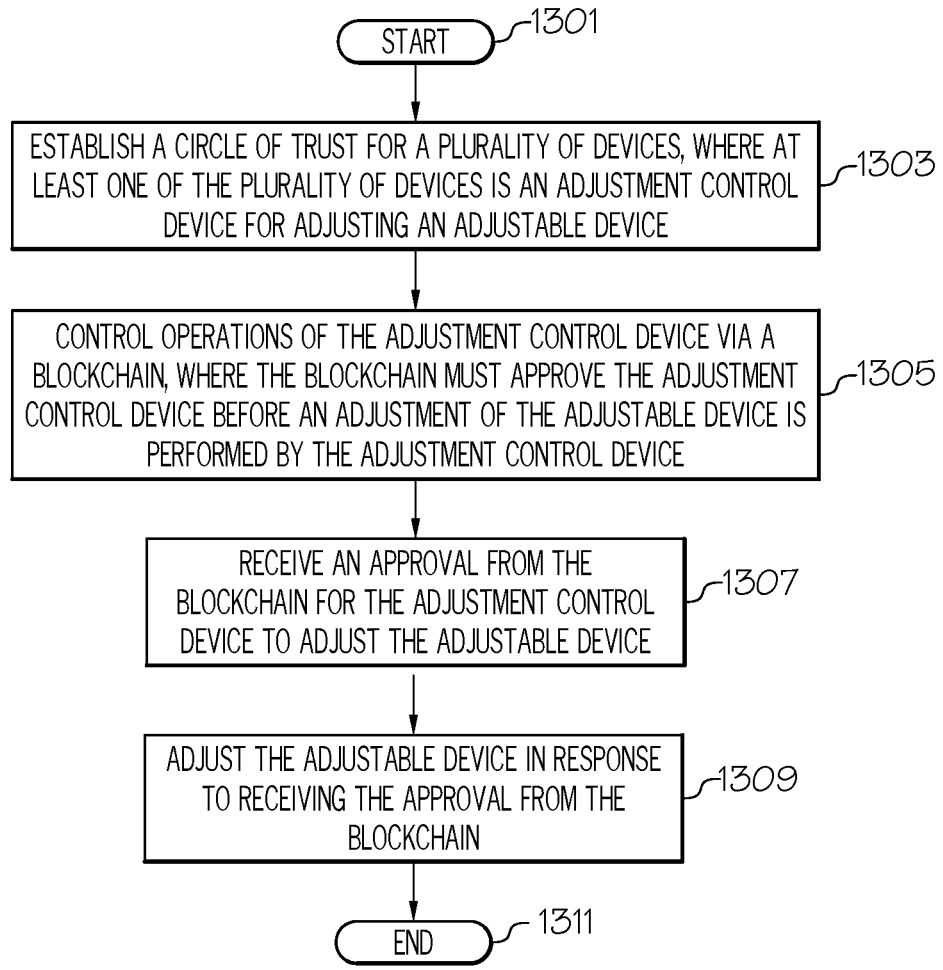
FIG. 13 is a high-level flow-chart of one or more steps performed in a processor-based method in accordance with one or more embodiments of the present invention.

FIG. 13 is a high-level flow-chart of one or more steps performed in a processor-based method in accordance with one or more embodiments of the present invention;

After initiator block 1301, a circle of trust (e.g., the circle of trust 904 shown in FIG. 9) is established (e.g., by one or more processors (e.g., processor(s) 103 shown in computer 101 in FIG. 1, which acts as supervisor for an adjustment control device within the circle of trust) for a plurality of devices as described in block 1303. That is, at least one of the plurality of devices is an adjustment control device for adjusting an adjustable device (e.g., patient pacemaker 953 shown in FIG. 9).

As described in block 1305, one or more processors control operations of the adjustment control device via a blockchain (e.g., blockchain environment 300 shown in FIG. 3, when implemented by the circle of trust). That is, the blockchain must approve the adjustment control device before an adjustment of the adjustable device is performed by the adjustment control device.

As described in block 1307, the processor(s) receive an approval to adjust the adjustable device from the blockchain, and then adjust the adjustable device in response to receiving the approval from the blockchain (block 1309).

The flow chart ends at terminator block 1311.

In an embodiment of the present invention, the adjustable device is a medical device (e.g., patient pacemaker 953 as shown in FIG. 9). In an embodiment in which the adjustable device is a medical device, one or more processors store patient information relating to the medical device as a set of data layers representing different data types in the blockchain (see FIG. 10).

In an embodiment of the present invention, the processor(s) store device data (e.g., device data 1008 shown in FIG. 10) about the adjustable device as a set of data layers representing different data types in the blockchain.

In an embodiment of the present invention, the set of data layers includes a device data layer that identifies the adjustable device, a performance data layer that describes a performance ability of the adjustable device, an environmental data layer that describes an environment of the adjustable device, a patient data layer that contains a medical history of a user of the medical device, and an emergency medical services data layer that describes emergency services provided to a user of the adjustable device (see FIG. 10). As described above and in an embodiment of the present invention, the environment of the adjustable device is a trusted network that is a member of the circle of trust.

In an embodiment of the present invention and as described above, the processor(s) send an alert to an Internet of Things (IoT) wearable that is a member of the plurality of devices in the circle of trust, where the alert describes an emergency medical condition detected by the medical device.

In one or more embodiments, the present invention is implemented using cloud computing. Nonetheless, it is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model includes at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but still is able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. In one or more embodiments, it is managed by the organization or a third party and/or exists on-premises or off-premises.

Community cloud: the cloud infrastructure is shared by several organizations and supports a specific community that has shared concerns (e.g., mission, security requirements, policy, and compliance considerations). In one or more embodiments, it is managed by the organizations or a third party and/or exists on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 14:
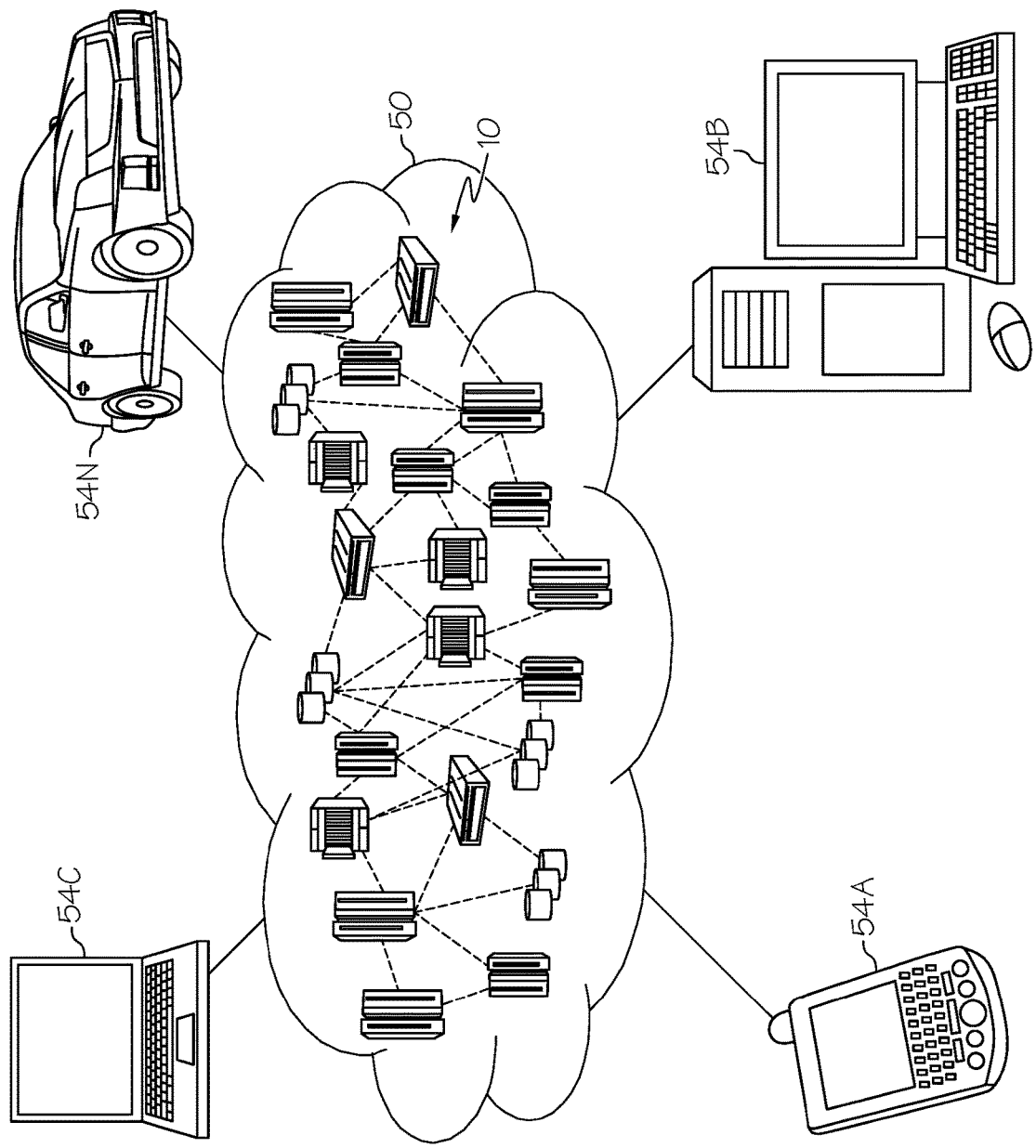
FIG. 14 depicts a cloud computing environment according to an embodiment of the present invention.

Referring now to FIG. 14, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N communicate with one another. Furthermore, nodes 10 communicate with one another. In one embodiment, these nodes are grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 14 are intended to be illustrative only and that computing nodes 10 and cloud computing environment 50 can communicate with any type of computerized device over any type of network and/or network addressable connection (e.g., using a web browser).

Figure 15:
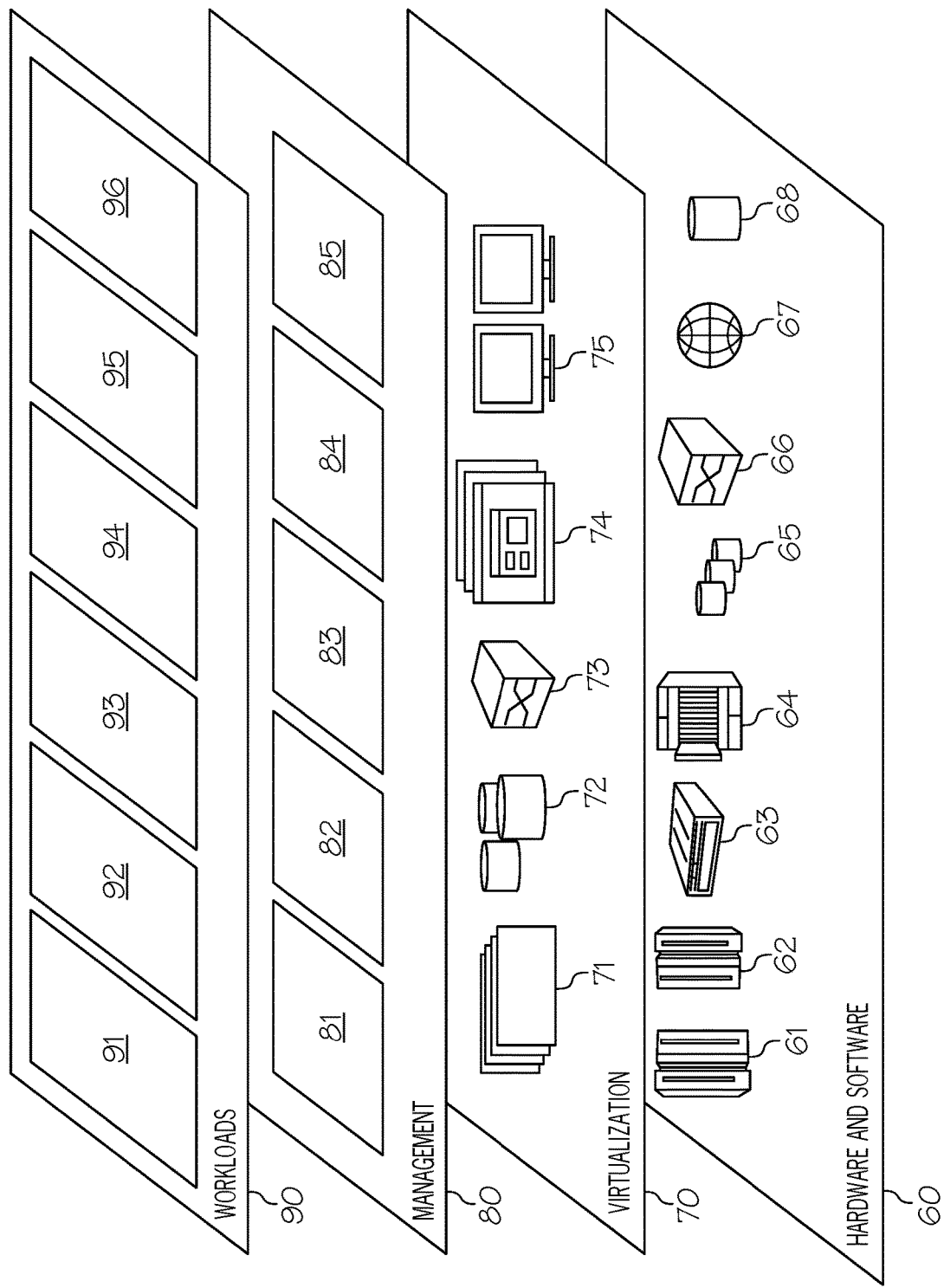
FIG. 15 depicts abstraction model layers of a cloud computer environment according to an embodiment of the present invention.

Referring now to FIG. 15, a set of functional abstraction layers provided by cloud computing environment 50 (FIG. 14) is shown. It should be understood in advance that the components, layers, and functions shown in FIG. 15 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities that are provided in one or more embodiments: virtual servers 71; virtual storage 72; virtual networks 73, including virtual private networks; virtual applications and operating systems 74; and virtual clients 75.

In one example, management layer 80 provides the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment are utilized in one or more embodiments. Examples of workloads and functions which are provided from this layer include: mapping and navigation 91; software development and lifecycle management 92; virtual classroom education delivery 93; data analytics processing 94; transaction processing 95; and device management processing 96, which performs one or more of the features of the present invention described herein.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

In one or more embodiments of the present invention, any methods described in the present disclosure are implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, in one or more embodiments of the present invention any software-implemented method described herein is emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
    establishing a circle of trust for a plurality of devices, wherein at least one of the plurality of devices is an adjustment control device for adjusting an adjustable medical device, and further wherein establishing the circle of trust includes:
        performing an initiation process for the adjustable medical device that includes registering patient information, including biometrics, and authentication of the patient as an owner of the adjustable medical device, and
        registering an adjustment control device and users of the adjustment control device that are authorized to adjust the adjustable medical device, wherein privileges to adjust the adjustable medical device granted to the users of the adjustment control device cannot be modified by the adjustment control device without re-authentication of the patient's biometrics and authorization by the adjustable medical device;
    controlling operations of the adjustment control device via a blockchain, wherein the blockchain must approve the adjustment control device before an adjustment of the adjustable medical device is performed by the adjustment control device;
    receiving a request from the adjustment control device to reprogram the adjustable medical device, wherein the request includes an adjustment command issued by the adjustment control device to reprogram the adjustable medical device from a first programmed state to a second programmed state;
    receiving an approval from the blockchain for the adjustment control device to reprogram the adjustable medical device from the first programmed state to the second programmed state, wherein the approval from the blockchain to reprogram the adjustable medical device from the first programmed state to the second programed state is based, at least in part, on the first programmed state included in the adjustment command issued by the adjustment control device matching a current authorized programmed state of the adjustable medical device included in the blockchain; and
    adjusting, by the adjustment control device, the adjustable medical device in response to receiving the approval from the blockchain, wherein adjusting the adjustable medical device programmatically changes a functionality of the adjustable medical device.

2. The method of claim 1, further comprising:
    storing, by one or more processors, patient information relating to the adjustable medical device as a set of data layers representing different data types in the blockchain.

3. The method of claim 2, further comprising:
    storing, by one or more processors, device data about the adjustable medical device as a set of data layers representing different data types in the blockchain.

4. The method of claim 3, wherein the set of data layers comprises a device data layer that identifies the adjustable medical device, a performance data layer that describes a performance ability of the adjustable medical device, an environmental data layer that describes an environment of the adjustable medical device, a patient data layer that contains a medical history of a user of the adjustable medical device, and an emergency medical services data layer that describes emergency services provided to a user of the adjustable medical device.

5. The method of claim 4, wherein the environment of the adjustable medical device is a trusted network that is a member of the circle of trust.

6. The method of claim 2, further comprising:
    sending, by one or more processors, an alert to an Internet of Things (IOT) wearable that is a member of the plurality of devices in the circle of trust, wherein the alert describes an emergency medical condition detected by the adjustable medical device.

7. The method of claim 1, wherein the plurality of devices in the circle of trust are peer nodes in a blockchain environment that controls the blockchain.

8. The method of claim 1, wherein only devices that are able to modify a functionality of the adjustable medical device are allowed to be part of the circle of trust.

9. The method of claim 1, wherein the adjustable medical device is a cardiac pacemaker in a patient's heart, and wherein the method further comprises:
    determining that the cardiac pacemaker is sending stimulation signals to the patient's heart at a rate that exceeds a predetermined level;
    in response to determining that the cardiac pacemaker is sending stimulation signals to the patient's heart at the rate that exceeds the predetermined level, automatically reducing the rate at which the cardiac pacemaker is sending stimulation signals to the patient's heart.

10. A computer program product for controlling a modification of an adjustable device, wherein the computer program product comprises a non-transitory computer readable storage device having program instructions embodied therewith, the program instructions readable and executable by a computer to perform a method comprising:
    establishing a circle of trust for a plurality of devices, wherein at least one of the plurality of devices is an adjustment control device for adjusting an adjustable medical device, and further wherein establishing the circle of trust includes:
        performing an initiation process for the adjustable medical device that includes registering patient information, including biometrics, and authentication of the patient as an owner of the adjustable medical device, and
        registering an adjustment control device and users of the adjustment control device that are authorized to adjust the adjustable medical device, wherein privileges to adjust the adjustable medical device granted to the users of the adjustment control device cannot be modified by the adjustment control device without re-authentication of the patient's biometrics and authorization by the adjustable medical device;
    controlling operations of the adjustment control device via a blockchain, wherein the blockchain must approve the adjustment control device before an adjustment of the adjustable medical device is performed by the adjustment control device;
    receiving a request from the adjustment control device to reprogram the adjustable medical device, wherein the request includes an adjustment command issued by the adjustment control device to reprogram the adjustable medical device from a first programmed state to a second programmed state;

receiving an approval from the blockchain for the adjustment control device to reprogram the adjustable medical device from the first programmed state to the second programmed state, wherein the approval from the blockchain to reprogram the adjustable medical device from the first programmed state to the second programed state is based, at least in part, on the first programmed state included in the adjustment command issued by the adjustment control device matching a current authorized programmed state of the adjustable medical device included in the blockchain; and adjusting, by the adjustment control device, the adjustable medical device in response to receiving the approval from the blockchain, wherein adjusting the adjustable medical device programmatically changes a functionality of the adjustable medical device.

11. The computer program product of claim 10, wherein the method further comprises:

storing patient information relating to the adjustable medical device as a set of data layers representing different data types in the blockchain.

12. The computer program product of claim 11, wherein the method further comprises:

storing device data about the adjustable medical device as a set of data layers representing different data types in the blockchain.

13. The computer program product of claim 12, wherein the set of data layers comprises a device data layer that identifies the adjustable medical device, a performance data layer that describes a performance ability of the adjustable medical device, an environmental data layer that describes an environment of the adjustable medical device, a patient data layer that contains a medical history of a user of the adjustable medical device, and an emergency medical services data layer that describes emergency services provided to a user of the adjustable medical device.

14. The computer program product of claim 13, wherein the environment of the adjustable medical device is a trusted network that is a member of the circle of trust.

15. The computer program product of claim 11, wherein the method further comprises:

sending an alert to an Internet of Things (IOT) wearable that is a member of the plurality of devices in the circle of trust, wherein the alert describes an emergency medical condition detected by the adjustable medical device.

16. The computer program product of claim 10, wherein the program instructions are provided as a service in a cloud environment.

17. A computer system comprising one or more processors, one or more computer readable memories, and one or more computer readable non-transitory storage mediums, and program instructions stored on at least one of the one or more computer readable non-transitory storage mediums for execution by at least one of the one or more processors via at least one of the one or more computer readable memories, the stored program instructions executed to perform a method comprising:

establishing a circle of trust for a plurality of devices, wherein at least one of the plurality of devices is an adjustment control device for adjusting an adjustable medical device, and further wherein establishing the circle of trust includes:

performing an initiation process for the adjustable medical device that includes registering patient information, including biometrics, and authentication of the patient as an owner of the adjustable medical device, and registering an adjustment control device and users of the adjustment control device that are authorized to adjust the adjustable medical device, wherein privileges to adjust the adjustable medical device granted to the users of the adjustment control device cannot be modified by the adjustment control device without re-authentication of the patient's biometrics and authorization by the adjustable medical device;

controlling operations of the adjustment control device via a blockchain, wherein the blockchain must approve the adjustment control device before an adjustment of the adjustable medical device is performed by the adjustment control device;

receiving a request from the adjustment control device to reprogram the adjustable medical device, wherein the request includes an adjustment command issued by the adjustment control device to reprogram the adjustable medical device from a first programmed state to a second programmed state;

receiving an approval from the blockchain for the adjustment control device to reprogram the adjustable medical device from the first programmed state to the second programmed state, wherein the approval from the blockchain to reprogram the adjustable medical device from the first programmed state to the second programed state is based, at least in part, on the first programmed state included in the adjustment command issued by the adjustment control device matching a current authorized programmed state of the adjustable medical device included in the blockchain; and adjusting, by the adjustment control device, the adjustable medical device in response to receiving the approval from the blockchain, wherein adjusting the adjustable medical device programmatically changes a functionality of the adjustable medical device.

18. The computer system of claim 17, wherein the method further comprises:

storing patient information relating to the adjustable medical device as a set of data layers representing different data types in the blockchain.

19. The computer system of claim 18, wherein the method further comprises:

storing device data about the adjustable medical device as a set of data layers representing different data types in the blockchain.

20. The computer system of claim 17, wherein the stored program instructions are provided as a service in a cloud environment.

* * * * *